United States Patent [19]
Guss et al.

[11] Patent Number: 6,100,055
[45] Date of Patent: *Aug. 8, 2000

[54] DNA ENCODING Fα-2M-BINDING PROTEIN AND PROTEIN ENCODED THEREBY

[76] Inventors: Bengt Guss, Dag Hamarskjölds väg 238B, S-756 52 Uppsala; Hans Jonsson, Börjegatan 58C, S-752 29 Uppsala; Martin Lindberg, Kornvägen 5, S-752 57 Uppsala; Hans-Peter Mueller, Tjälinge 9, S-740 20 Brunna, all of Sweden; Liisa K. Rantamäki, Ojahaanpolku 6 B 20, FIN-016 00 Vantaa, Finland

[*] Notice: This patent issued on a continued prosecution application filed under 37 CFR 1.53(d), and is subject to the twenty year patent term provisions of 35 U.S.C. 154(a)(2).

[21] Appl. No.: 08/669,408

[22] PCT Filed: Sep. 6, 1994

[86] PCT No.: PCT/SE94/00826

§ 371 Date: Jul. 3, 1996

§ 102(e) Date: Jul. 3, 1996

[87] PCT Pub. No.: WO95/07296

PCT Pub. Date: Mar. 16, 1995

[30] Foreign Application Priority Data

Sep. 6, 1993 [SE] Sweden .................................. 9302855

[51] Int. Cl.[7] .......................... C12N 15/11; C12N 15/63; C07K 14/315
[52] U.S. Cl. ...................... 435/69.1; 435/71.1; 435/71.2; 435/252.3; 435/254.11; 435/320.1; 435/471; 536/23.7; 530/350
[58] Field of Search ................................ 435/69.1, 252.3, 435/254.11, 320.1, 71.1, 71.2, 471, 325; 536/23.7; 935/58; 530/350

[56] References Cited

U.S. PATENT DOCUMENTS 5,116,964  5/1992  Capon et al. .............................. 536/27

OTHER PUBLICATIONS

Barrett et al. The electrophoretically 'slow' and 'fast' forms of the $\alpha_2$-macroglobulin molecule. Biochemical Journal. vol. 181, pp. 401–418, 1979.

Björck et al. Streptococcal protein G, expressed by streptococci or by *Escherichia coli*, has separate binding sites for human albumin and IgG. Molecular Immunology. vol. 24, No. 10, pp. 1113–1122, Oct. 1987.

Gettins et al. Preparation and initial characterization of an intermediate, half–cleaved form of human $\alpha_2$-macroglobulin. Biochemistry. vol. 28, pp. 5613–5618, 1989.

Guss et al. Structure of the IgG–binding regions of streptococcal protein G. EMBO Journal. vol. 5, No. 7, pp. 1567–1575, Jul. 1986.

Jonsson et al. MAG, a novel plasma protein receptor from Streptococcus dysgalactiae. Gene. vol. 143, pp. 85–89, May 27, 1994.

Jonsson et al. The type–III Fc receptor from Streptococcus dysgalactiae is also an $\alpha_2$-macroglobulin receptor. European Journal of Biochemistry. vol. 220, pp. 819–826, Mar. 15, 1994.

Justus et al. Quantification of free $\alpha_2$-macroglobulin and $\alpha_2$-macroglobulin-protease complexes by a novel ELISA system based on streptococcal $\alpha_2$-macroglobulin receptors. Journal of Immunological Methods. vol. 126, pp. 103–108, 1990.

Sjobring et al. Ig–binding bacterial proteins also bind proteinase inhibitors. The Journal of Immunology. vol. 143, No. 9, pp. 2948–2954, Nov. 1, 1989.

Guss et al, EMBO Journal, vol. 5, No. 7, pp. 1567–1575, Jul. 1986.

Strickland et al., *J. Biol. Chem.*, vol. 265, No. 29, pp. 17401–17404 (1990).

Chatwal et al., *J. Bacteriol.*, vol. 169, No. 8, pp. 3691–3695 (Aug. 1987).

Eaton et al., *Cell Biochem. Funct.*, vol. 7, No. 1, pp. 57–64 (Jan. 1989) (Abstract).

*Primary Examiner*—Prema Mertz
*Attorney, Agent, or Firm*—Foley & Lardner

[57] ABSTRACT

DNA molecules and methods for producing proteins, or fragments thereof, having binding activity for the fast form of $\alpha_2$-macroglobulins as exemplified for the streptococcal surface proteins MIG, MAG and ZAG.

28 Claims, 12 Drawing Sheets

FIG. 4A

```
AAGCTTTATTTATTATAAAAGAAAGTAATTTTGAAAAATTATAGAAAAATCACTTTTATGCTAATAAAATAGCCATAAATATAAATTGATGAGTCTATGATAGGAGATTTATTTGCCAG   120

GATTTCCTAATTTTATTAATTTAACGAAAAATTAAATGAAATCCTTGATTTAATTTTGTTAAGTTGTATAATAAAAGGTGAAATTGAAGTTAGTTTCAAATTTTT   240
                                                                     -S

TGGTTTTTTAATATGTGCTGGCGTATTAAATAAAAAAAGGAGAAAGTAATGGAAAAAGAAAAAAAAGTAAATACTTTTACGTAAATCAGCTTTTGGATTAGGTCCGATCAGCTGCGT   360
                                                -α, -M                        M  E  K  K  V  K  Y  F  L  R  K  S  A  F  G  L  A  S  V  S  A  A    24

TTTTAGTTGGGACTGCGGTAGTAAATGCGGAAGAGTCAACTGTTTCGCCTGTGACAGTTGCTACAGATGCAGTTACTACTTCTAAGGAAGCGCTTGCGATAATTAACAAGCTAAGTGAAG   480
 F  L  V  G  T  A  V  V  N  A  E  E  S  T  V  S  P  V  T  V  A  T  D  A  V  T  T  S  K  E  A  L  A  I  I  M  K  L  S  E    64

ATAATTTAAAATAATCTTGACATCCAGGAAGTATTGGCCAAAGCGGGGAGGGACATTTTAGCCTCTGACTCAGCAGATACTATCAAAGCACTTCTTGCTGAAGTTACCGCTGAAGTTACTC   600
 D  N  L  K  I  L  T  S  R  K  Y  W  P  K  R  G  R  T  L  A  S  D  S  A  D  T  I  K  A  L  L  A  E  V  T  A  E  V  T    104

GTTTGAATGAGGAAAAAGATGCACGTGATGCAGTAGACAAAGCTATTGCAGCAGATGCAGCCGCTTTTTCTGAATTAAAAGATGCTCAACTGAAAGCATATGAAGATCTTGCGAAACTCG   720
 V  E  M  E  E  K  D  A  R  D  A  V  D  K  A  I  A  A  D  A  A  A  F  S  E  L  K  D  A  Q  L  K  A  Y  E  D  L  A  K  L    144

```
CAGCAGATACAGACTTAGATTAGATGTTGCTAAAATTATAAATGACTACACTACAAAAGTTGAAAATGCAAAAACAGCAGAAGATGTTAAAAAAATTTTTGAAGAATCTCAAAATGAAG        840
 A  A  D  T  D  L  D  L  D  V  A  K  I  I  M  D  Y  T  T  K  V  E  N  A  K  T  A  E  D  V  K  K  I  F  E  E  S  Q  M  E         184
        - Alb
TGACACGTATTAAACAGAAAAAGCTTAAAAGCTGCAGCACTAGCTAAAGCAAAAGCAGATGCTATTGAAATTCTGAAGAAATACGGAATTGGCGATTACTATATTAAATTAATTAATA         960
 V  T  K  I  K  T  K  K  A  L  K  A  A  A  L  A  K  A  K  A  D  A  I  E  I  L  K  K  Y  G  I  G  D  Y  Y  I  K  L  I  N         224
                                                                        - IgG
ATGGTAAAAACTGCAGAAGGTGTGACTGCTCTTAAAGATGAAATTTTAGCTTCAAAGCCACCTGAATTGACGCCACCTGAATTAACACCAGCTTTGACAACCTACAAACTTGTTATCAATG       1080
 M  G  K  T  A  E  G  V  T  A  L  K  D  E  I  L  A  S  K  P  A  V  I  D  A  P  E  L  T  P  A  L  T  T  Y  K  L  V  I  N         264
GTAAAAACATTGAAAGGCGAAACTACTACTAAAGCAGTAGACGCAGAAACTGCAGAAAAAGCTTCAAAGATACGCTAAGAAACGGTGTTGATGGTGTTTGGACTTACGATGATGCCGA        1200
 G  K  T  L  K  G  E  T  T  T  K  A  V  D  A  E  T  A  E  K  A  F  K  Q  Y  A  N  E  N  G  V  D  G  V  W  T  Y  D  D  A         304
CTAAGACCTTTACTGTAACTGAAATGGTTACTGAAGTTCCTGGTGATGCACCAACTGAACCAAAAAAACCAGAAGCAAGTATCCCTCTTGTTCCGTTAACTCCTGCAACTCCAATTGCTA       1320
 T  K  T  F  T  V  T  E  M  V  T  E  V  P  G  D  A  P  T  E  P  K  K  P  E  A  S  I  P  L  V  P  L  T  P  A  T  P  I  A         344
AAGAGACGCCTAAGAAGAAGAAGATACTAAGAAGAAGATGCTAAAAAAGAAGCTAAGAAAGAAGAAGCTAAGAAAGAAGAAGCTAAGAAAGCTGCAACTCTTCCTACAACTGGTGAAG       1440
 K  D  D  A  K  K  D  D  T  K  K  E  D  A  K  K  P  E  A  K  K  E  E  A  K  K  A  A  T  L  P  T  T  G  F                         384
GAAGCAACCCATTCTTCACAGCTGCTGCCGCTTGCAGTAATGGCTGGTGCGGGTGCTTTGGCAGTCGCTTCAAAACGTAAAGAAGACTAATTGTCATTGCTTTTGACAAAAAGCTT         1555
 G  S  N  P  F  F  T  A  A  A  L  A  V  M  A  G  A  G  A  L  A  V  A  S  K  R  K  E  D  .                                        413
```

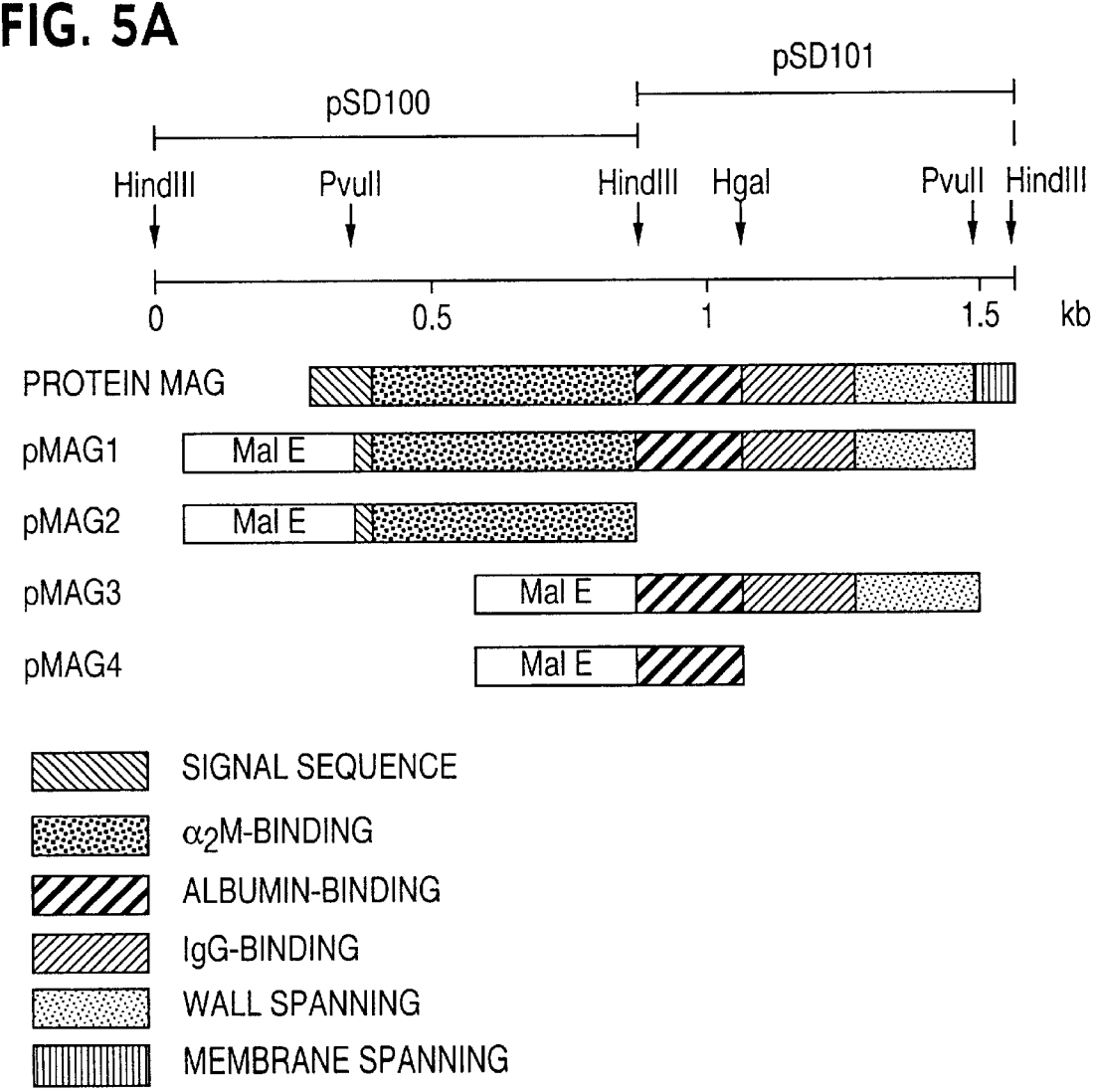

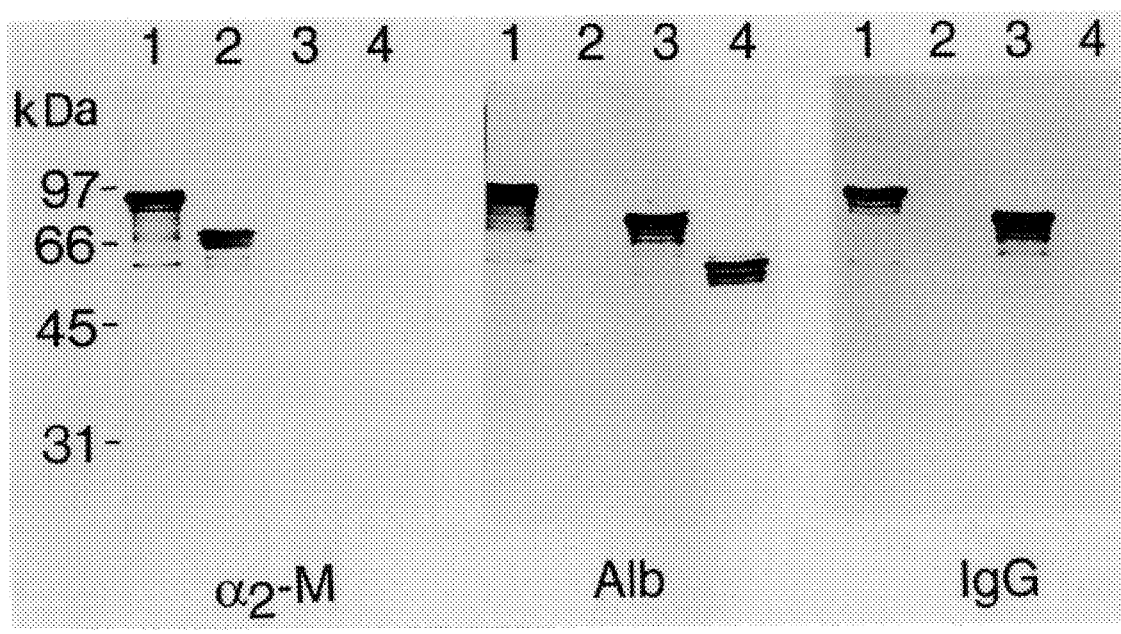

FIG. 6

```
         10        20        30        40        50        60
          |         |         |         |         |         |
TCTTCAGTGGGTGCTCTAGATGCTACAACGGTGTTAGAGCCTACAACAGCCTTCATTAGA
  S  S  V  G  A  L  D  A  T  T  V  L  E  P  T  T  A  F  I  R 70        80        90       100       110       120
          |         |         |         |         |         |
GAGGCTGTTAGGGAAATCAATCAGCTTAGTGATGACTACGCTGACAATCAAGAGCTTCAG
  E  A  V  R  E  I  N  Q  L  S  D  D  Y  A  D  N  Q  E  L  Q 130       140       150       160       170       180
          |         |         |         |         |         |
GCTGTTCTTGCTAATGCTGGAGTTGAGGCACTTGCTGCAGATACTGTTGATCAAGCCAAA
  A  V  L  A  N  A  G  V  E  A  L  A  A  D  T  V  D  Q  A  K 190       200       210       220       230       240
          |         |         |         |         |         |
GCAGCTCTTGACAAAGCAAAGGCAGCTGTTGCTGGTGTTCAGCTTGATGAAGCAAGACGT
  A  A  L  D  K  A  K  A  A  V  A  G  V  Q  L  D  E  A  R  R 250       260       270       280       290       300
          |         |         |         |         |         |
GAGGCTTACAGAACAATCAATGCCTTAAGTGATCAGCACGAAAGCGATCAAAAGGTTCAG
  E  A  Y  R  T  I  N  A  L  S  D  Q  H  E  S  D  Q  K  V  Q 310       320       330       340       350       360
          |         |         |         |         |         |
CTAGCTCTAGTTGCTGCAGCAGCTAAGGTGGCAGATGCTGCTTCAGTTGATCAAGTGAAT
  L  A  L  V  A  A  A  A  K  V  A  D  A  A  S  V  D  Q  V  N 370       380       390       400       410       420
          |         |         |         |         |         |
GCAGCCATTAATGATGCTCATACAGCTATTGCGGACATTACAGGAGCAGCCTTGTTGGAG
  A  A  I  N  D  A  H  T  A  I  A  D  I  T  G  A  A  L  L  E 430       440       450       460       470       480
          |         |         |         |         |         |
GCTAAAGAAGCTGCTATCAATGAACTAAAGCAGTATGGCATTAGTGATTACTATGTGACC
  A  K  E  A  A  I  N  E  L  K  Q  Y  G  I  S  D  Y  Y  V  T 490       500       510
          |         |         |
TTAATCAACAAAGCCAAAACTGTTGAAGGTGTCAATGCG
  L  I  N  K  A  K  T  V  E  G  V  N  A
```

FIG. 7A

```
AAGCTTCACAGGTATTCACCAGTAGATGCTTTTGTGGTCTTATTGACACGCACTTGTGGCGAGAGTACTGAAACTAAAGCGAAAAACGAACTACTATAAAAGAATATTAGTCAAGCG  120

TTGGGAGATATTCCTAACGTTTTTTGACAAAAATGATTGATCTCTGTTACGAAATAAATAAAGGTGATATTGACAGAAATCCCATTTTATAAAACTTTATTTATTATTATAAAAG  240

AAAGTAATTTTTGAAAAATTATAGAAACCACTTTTATGCTAATAAAATATAAAATGATGAGTCTATGATAGGAGATTTATTTGCCAGGATTTCCTAATTTTATTAATTT  360

AACGAAAAATTGATAGAAAATTAAATGAAATCCTTGATTTAATTTGTTAAGTTGTATAATAAAAGGTGAAATTATTAGATTGTAGTTCAAATTTTTGCTTTTTTAATATGTGCTGGC  480
                         S
                         ↑
GTATTAAATAAAAAAGGAGAAAAGTAATGGAAAAAGAAAAGTAAATACTTTTTACGTAAATCAGCTTTTGGATTAGCGTCTGTATCAGCTGGTTTTAGTTCGGGAGCACTAGA  600
                  _____   M  E  K  K  V  K  Y  F  L  R  K  S  A  F  G  L  A  S  V  S  A  A  F  L  V  S  G  A  L  E   32

AAATACTATAACTGTTTCTGCAGAAACTATACCTGCAGCGGTCATTGTACCTGTTGGCCTAGATACACAGAATTACAAAAATGGTAGCATTGCAAATGATTGCAGACTGACAA  720
 N  I  T  V  S  A  E  T  I  P  A  A  V  I  V  P  V  G  L  D  T  T  E  L  Q  K  W  Y  D  I  A  N  D  L  V  A  T  D  N   72

TGCTACTCCGGGAGGCGTATTTACAGCAGACTCAATGAAGGCATTATATCGTTTACTAAATGATGCATACGATGTTGTTGGAATCAAAAGACTATAGAAAATGATTCTCAAGATAGGAT  840
 A  T  P  G  G  V  F  T  A  D  S  M  K  A  L  Y  R  L  L  N  D  A  Y  D  V  L  E  S  K  D  Y  R  K  Y  D  S  Q  D  R  I  112

TGTTGAATTGGTAAACAATTAAAGAATACTACGCCAGTATTTGATACTACTCGCTTGAATACCTGGTATGATGCTAATGAAATTGT  960
 V  E  L  V  N  N  L  K  M  T  T  Q  S  L  L  P  I  G  V  E  P  V  V  F  D  T  T  R  L  N  T  W  Y  D  A  A  N  E  I  V  152
```

```
GACTACTTACAAACTTATTGTTAAAGGTAACACTTTCTCAGGGGAAACATGCAGAAAAAGCCTAGACCGGAAACTGCAGAAAAAGCCTAGACCGGAAACTGCAGAAAAAGCCTAACGAAAAAGCGTGTTTA 1920
     T  T  Y  K  L  I  V  K  G  N  T  F  S  G  E  T  T  T  K  A  V  D  A  E  T  A  E  K  A  F  K  Q  Y  A  N  E  N  G  V  Y  472
                                                              ↑ IgG 5
CGGTGAATGGTCTTATGACGATGCAACTAAAAACCTTTACAGTTACTGAAAAACCAGTGCAGTGATTGACCCACCTGAATTAACCACCAGCATTGACCGCATTGTTATCAATGGTAA 2040
     G  E  W  S  Y  D  D  A  T  K  T  F  T  V  T  E  K  P  A  V  I  D  A  P  E  L  T  P  A  L  T  T  Y  K  L  V  I  N  G  K  512

AACATTGAAAGGCGAAACAACTAAAGGCAGTAGACGCAGAAACTGCAGAAAAAGCCTCAAACAATACGCTAACGAAAAAGCCAGAAGCAAGTATCCCTCTTGTTCCGTAACTCCTGCAACTCCAATTGCTAAAGA 2160
     T  L  K  G  E  T  T  T  K  A  V  D  A  E  T  A  E  K  A  F  K  Q  Y  A  N  E  N  G  V  D  G  V  W  T  Y  D  D  A  T  K  552
                                                              ↑ W

GACCTTTACGGTAACTGAAATGGTTACTGAAGTTCCTGGTGATGCACCAACTGAACCAGAAAAGCCAGAAGCAAGTATCCCTCTTGTTCCGTAACTCCTGCAACTCCAATTGCTAAAGA 2280
     T  F  T  V  T  E  M  V  T  E  V  P  G  D  A  P  T  E  P  E  K  P  E  A  S  I  P  L  V  P  L  T  P  A  T  P  I  A  K  D  592

TGACGCTAAGAAAGACGATACTAAGAAAGTCGATACTAAGAAAGAAGAGCTAAGAAAAACCAGAAGCTAAGAAGAAGAAGAGTAAGAAGAAGAAGCTAAGAAAGAAGAAGCTAAGAAGGAAGCTAAGAAGGCTAACTCTTCCTAC 2400
     D  A  K  K  D  D  T  K  K  V  D  T  K  K  E  D  A  K  K  P  E  A  K  K  E  E  A  K  K  E  E  A  K  K  A  A  T  L  P  T  632
                                                              ↑ M

AACTGGTGAAGGAAGCAACCCATTTTTCACAGCTGCTGCGCTTGCAGTAATGGCTGGCGGGTGCTTGGCAGTGCTTCAAAACGTAAAGAGACTAATTGTCATTGCTTTTGACAAA 2520
     I  G  E  G  S  N  P  F  F  T  A  A  A  L  A  V  M  A  G  A  G  A  L  A  V  A  S  K  I  K  E  D  .    664

AAGCTT                                                                                                                          2526
```

DNA ENCODING Fα-2M-BINDING PROTEIN AND PROTEIN ENCODED THEREBY

This application is a national phase application of PCT/SE94/00826, filed Sep. 6, 1994.

The invention relates to the field of gene technology and is concerned with recombinant DNA molecules, which contain nucleotide sequences coding for different proteins or polypeptides which have the ability to specifically bind to $\alpha_2$-macroglobulin ($\alpha_2$M), a plasma proteinase inhibitor. The invention also comprises microorganisms containing the aforesaid molecules, and the use thereof in the production of the aforesaid proteins or polypeptide.

BACKGROUND OF THE INVENTION

The existence of bacteria that bind specifically to the plasmaproteinase inhibitor $\alpha_2$M has earlier been reported (Müller and Blobel 1983; 1985). The binding of $\alpha_2$M to streptococci is highly specific and streptococci of different serological groups or species bind the two different conformational forms of this plasma proteinase inhibitor referred to as "slow" (s$\alpha_2$M) and "fast" (f$\alpha_2$M) based on their electrophoretical behaviour (Müller and Blobel 1983; 1985). The slow form represents the native inhibitor and the fast form the inhibitor/protease complex (Barret et al. 1979). In 1989 Sjöbring et al. reported that both conformational forms of $\alpha_2$M could be bound to the protein G. This receptor is one of the best studied so called type III Fc receptors (Björck and Åkerström 1990, Sjöbring et al. 1989a, Sjöbring el al. 1991). The gene encoding protein G has been cloned and sequenced (Guss et al. 1986; Olsson et al. 1987) and binding properties been studied (Guss et al. 1986; Björck et al. 1987; Åkerström et al. 1987; Nygren et al. 1988). As a result of these studies it has been shown that protein G binds both IgG and serum albumins through specific domains in the protein. Sjöbring et al. 1989b reported that in addition of binding these two serum proteins protein G should also bind to both conformational forms of $\alpha_2$M. The latter binding they reported should be located in the IgG binding domain of protein G,—a finding that will be contradicted in the present application. The quantification of free $\alpha_2$M and $\alpha_2$M-protease complexes using streptococcal $\alpha_2$M receptors have been described (Justus et al. 1990). Also in studies concerning purification and characterisation of $\alpha_2$M from mastitis milk these streptococcal receptors have been used (Rantamäki and Müller 1992). In these cases intact streptococcal cells have been used as the source of the receptor. Therefore a protein which for instance binds specifically to $\alpha_2$M should be of great biotechnological interest. This protein could in analogy to what Nygren et al. 1988 reported be immobilized and used to affinity purify away any undesired $\alpha_2$M in the sample. Furthermore different proteins (or fragments thereof) with $\alpha_2$M-binding activity could be used to detect and measure the amount of $\alpha_2$M in a sample. Generally it may be difficult to obtain a homogeneous and reproducible product if such receptors should be prepared from streptococcal cells directly. Moreover, most streptococci are pathogenic and need complex culture media which involve complications in large-scale cultures. There is thus a need for a new method for producing $\alpha_2$M-binding proteins (or fragments thereof).

SUMMARY OF THE INVENTION

The present invention relates to different recombinant DNA molecules comprising nucleotide sequences which code for proteins or polypeptides having $\alpha_2$M-binding activity. The natural source of the nucleotide sequences encoding the $\alpha_2$M-binding activity is the *S. dysgalactiae* strain SC1 and/or 8215 respectively, and or the *Streptococcus equi* subsp. *zooepidemicus* strain V, but with the knowledge of the respective nucleotide and the deduced amino acid sequences presented here the gene(s) or parts of the gene(s) can be made synthetically or reisolated. In particular the knowledge of the deduced amino acid sequence covering the part of the gene encoding the $\alpha_2$M-binding activity can be used to produce (synthetical) polypeptides which retain or inhibit the $\alpha_2$M-binding. These polypeptides can be labelled with various compounds such as enzymes, flourescent dyes, biotin (or derivatives thereof), radioactivity etc. and used in diagnostic tests such as ELISA or RIA techniques.

BRIEF DESCRIPTION OF THE DRAWINGS

FIGS. 4A and 4B. Nucleotide sequence of the mag gene form *S. dysgalactiae* strain 8215 and the deduced aa sequence (SEQ ID NOS:9 and 10). Underlined, the putative transcription initiation signals. The ribosome binding site is double underlined. The start of the signal sequence (S), $\alpha_2$M-, Albumin- (Alb) and IgG-binding domains, respectively, are indicated as well as the cell wall binding (W) and membrane spanning (M) regions. In the C-terminal the LPXTGX motif is underlined. The nucleotide sequence was determined for both DNA strands by the dideoxy chain-termination method of Sanger et al. (1977). The juxtaposition in lambda SD1 of the inserts in pSD100 and pSD101 was verified using oligonucleotide primers (hybridizing on both sides of the HindIII site) allowing sequencing over the HindIII site in position 862. Sequence reactions were performed using "Sequenase, version 2.0" kit (United States Biochemical Corporation, Cleveland, Ohio, USA). The obtained nucleotide sequence were analyzed using the PC/GENE computer software package, Intelligenetics Inc. CA, USA.

FIGS. 5A–5C. (A) Schematic presentation of protein products coded by the expression clones PMAG 1–4 derived from S. dysgalactiae, strain 8215. Restriction sites used in the construction work are indicated. The two upper lines represent inserts of streptococcal DNA in pSD100 and pSD101. The upper bar represents protein MAG. (The Mal E portion is not drawn to scale). (B) SDS-PAGE of total cell lysates from clones harbouring pMAG1–4. Lanes: (M) molecular size markers, lanes 1–4 correspond to lysates from E. coli pMAG1–4, respectively. Methods: After IPTG induction the cells were harvested, lysed and protein samples were subjected to SDS-PAGE by the method of Laemmli (1970) using a 4% spacer and 12% separation gel. After electrophoresis the gel was stained with Coomassie Brilliant Blue, destained photographed. (C) Western-blot analysis of the proteins encoded by pMAG1–4. Three parallel gels were run using the same conditions as described in the legend to FIG. 5(B). After the electrophoresis the proteins were electrophoretically transferred to nitrocellulose membranes. The membranes were washed and blocked in a PBS-T solution and separately incubated with horseradish peroxidase labelled bovine f$\alpha_2$M, goat albumin and polyclonal goat IgG, respectively. After incubation for one hour at room temperature the membranes were washed with PBS-T and the bound labelled serum proteins were visualized by the addition of a 4-chloro-1-naphtol solution.

FIG. 6. Nucleotide sequence and deduced amino acid sequence (SEQ ID NOS: 7 and 8) of the zag gene (from Streptococcus zooepidemicus) encoding f$\alpha_2$M-binding activity.

FIGS. 7A through 7C show the nucleotide sequence and deduced amino acid sequence (SEQ ID NOS:1 and 2) of the cloned mig gene from Streptococcus dysgalactiae, strain SC1. Features of the sequence are indicated as follows: underlined nucleotide sequences represent possible promoter signals, double underlined nucleotide sequence represents the ribosome binding site, underlined amino acid sequence marks a hexapeptide matching the putative wall anchoring (SEQ ID NO:12) LPXTGX consensus, s represents the start of the signal sequence, IgG1–IgG5 represent the IgG-binding, 70 aa long repeat units, W represents the cell wall spanning region, M represents the membrane spanning domain.

DESCRIPTION OF THE PREFERRED EMBODIMENTS

Figure 1:
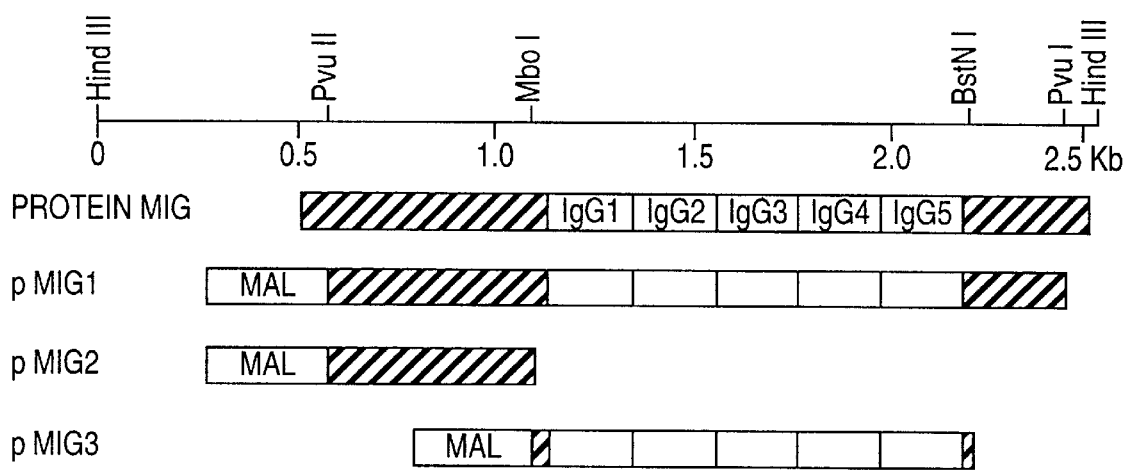
FIG. 1. Restriction map of the Hind III restriction fragment containing the mig gene from *Streptococcus dysgalactiae*, strain SC1 and schematic drawings of the various fusion protein products. The upper line indicates the position of the restriction sites used in the construction of the various expression clones. The upper bar represents the native MIG protein with the binding activities indicated. The other three bars represent the protein products encoded by the expression clones PMIG 1–3.

For producing a recombinant DNA molecule according to the invention a suitable cloning vehicle or vector, for example a plasmid or phage DNA, may be cleaved with the aid of restriction enzymes whereupon the DNA sequence coding for the desired protein or polypeptide is inserted into the cleavage site to form the recombinant DNA molecule. This general procedure is known per se, and various techniques for cleaving and ligating DNA sequences have been described in the literature (see for instance U.S. Pat. No. 4,237,224; Ausubel et al. 1991; Sambrook et al. 1989); but to our knowledge these techniques have not bee used in the present protein system. If the S. dysgalactiae strains SC1, 8215, or the S. equi subsp. zooepidemicus are employed as the source of the desired nucleotide sequences it is possible to isolate said sequences and to introduce them into suitable vectors in a manner such as described in the experimental part below or since the nucleotide sequences are presented here use a polymerase chain reaction (PCR)-technique to obtain the complete genes or fragments of the mig, mag, or zag genes.

Hosts that may be employed- that is, microorganisms which are caused to produce the proteins or active fragments thereof—may comprise bacterial hosts such as strains of e. g. Escherichia coli, Bacillus subtilis, Streptococcus sp., Staphylococcus sp., Lactobacillus sp. and furthermore yeasts and other eucaryotic cells in culture. For obtaining maximum expression, regulatory elements such as promoters and ribosome-binding sequences may be varied in a manner known per se. The protein or active protein thereof can be produced intra- or extracellular. To obtain good secretion in various bacterial systems different signal peptides can be employed. To facilitate the purification and/or detection of the protein or fragment thereof, they could be fused to an affinity handle and/or enzyme. This can be done on both genetical and protein level. To modify the features of the protein or polypeptide thereof the gene or parts of the gene can be modified by e.g. in vitro mutagenesis; or by fusion with other nucleotide sequences which encode polypeptides resulting in fusion proteins with new features.

The invention thus comprises recombinant DNA molecules containing a nucleotide sequence which codes for a protein or polypeptide having a $\alpha_2$M-binding activity. Furthermore, the invention comprises vectors such as plasmids and phages containing such a nucleotide sequence, and organisms, especially bacteria e.g. strains of E.coli, B.subtilis Streptococcus sp. and Staphylococcus sp., into which such a vector has bee introduced. Alternatively, such a nucleotide sequence may be integrated into the natural gene material of the microorganism.

The application furthermore relates to methods for the production of proteins or polypeptides having the $\alpha_2$M-binding activity of protein MIG, MAG, ZAG or active fragments thereof. According to this method, a microorganism as set forth above is cultured in a suitable medium whereupon the resultant product is isolated by affinity chromatographic purification with the aid of IgG or albumin bound to an insoluble carrier, or by means of some other separating method, for example ion exchange chromatography.

Vectors, especially plasmids, which contain the respective protein MIG, MAG or ZAG encoding nucleotide sequences or parts thereof may advantageously be provided with a readily cleavable restriction site by means of which a nucleotide sequence that codes for another product can be fused to the respective protein MIG, MAG or ZAG encoding nucleotide sequence, in order to express a so called fusion protein. The fusion protein may be isolated by a procedure utilising its capacity of binding to f$\alpha_2$M and/or IgG, whereupon the other component of the system may if desired be liberated from the fusion protein. This technique has been described at length in WO 84/03103 with respect to the protein A system and is applicable also in the present context in a analogous manner. The fusion strategy may also be used to modify, increase or change the f$\alpha_2$M binding activity of the MIG, MAG and ZAG proteins or f$\alpha_2$M binding parts thereof by combining them in various combinations or with other $\alpha_2$M binding proteins.

Starting Materials

Bacterial strains and cloning vectors

Streptococcus dysgalactiae strain 8215 and Streptococcus equi subsp. zooepidemicus strain V were obtained from The National Veterinary Institute, Uppsala, Sweden. The S. dysgalactiae strain SC1 was obtained from Dr Rantamäki, Dep. of Microbiology and Epizoology, College of Veterinary Medicine, Helsinki, Finland.

E.coli strain DH5α was used as bacterial host for the plasmids to be constructed. E. coli strain P2392 was used in cloning with the lambda vector EMBL3 (Frischauf et al., 1983) and as a host for expression of the lambda SD1 or lambda SZG1 encoded plasmaprotein-binding proteins, termed protein MAG and protein ZAG.

The lambda EMBL3 vector, *E. coli* strain P2392 and in vitro packaging extract (Gigapack ®II gold) were otained from Stratagene, La Jolla, Calif., USA. The plasmid vector pGEM11zf(+) was obtained from Promega, Madison, Wis. USA. A protein fusion and purification system obtained from NewEngland Biolabs, USA was used to construct clones expressing various parts of the mig, mag or zag genes fused to the vector pMALC2. This system was used to construct the expression clones pMIG1–3 pMAG1–4, and pZAG1–2. The system was used essentially according to the manufacturers recommendations but the host strain was *E. coli* strain DH5α.

All strains and plasmid- or phage-constructs used in the examples are available at the Department of Microbiology at the Swedish University of Agricultural Sciences, Uppsala, Sweden.

Buffers and media

*E. coli* was grown on LB (Luria Bertani broth) agar plates or in LB broth (Sambrook et al., 1989) at 37° C. Ampicillin was in appropriate cases added to the *E. coli* growth media to a final conc. of 50 μg/ml. The streptococci were grown at 37° C. on bloodagar-plates (containing 5% final conc. bovine blood) or in Todd-Hewitt broth (obtained from Oxoid, Ltd Basingstoke, Hants., England) supplemented with Yeast Extract (Oxoid) to a final conc. of 0.6%. PBS: 0,05M sodium phosphate pH 7,1; 0,9% NaCl. PBS-T: PBS supplemented with TWEEN 20 to a final conc. of 0,05%.

Preparation of DNA from Streptococci

Streptococci of resp. strains and species were grown separately overnight in Todd-Hewitt Broth supplemented with 0.6% yeast extract and 10 mM glycine. The next morning glycine was added to a conc. of 0.067 M and the incubation was continued at 37° C. for additional 2 h. After harvest the cells were washed three times in a buffer consisting of 50 mM Tris-HCl pH 7.0+50 mM EDTA and resuspended to a ¹⁄₂₀ of the original culture volume in the same buffer including 25% sucrose. Lysozyme (Boehringer, Germany) was added to a final conc. of 30 mg/ml and the suspension was incubated with gentle agitation for 2 h at 37° C. The cells now converted to protoplasts were then pelleted by centrifugation and resuspended in buffer consisting of 50 mM Tris-HCl pH 7.0+50 mM EDTA including 1% SDS (sodium dodecyl sulphate) and incubated at 65° C. for 15 min. Cell debris was removed by centrifugation and the viscous supernatant further treated as described for chromosomal DNA preparations (Sambrook et al. 1989).

Proteins and other reagents

Human IgG (Gammaglobin, KabiVitrum, Stockholm) was absorbed to protein A Sepharose (Pharmacia LKB Biotechnology, Uppsala, Sweden), and after elution with glycine HCL buffer, pH 2.8, immediately neutralised and then dialysed against PBS, pH 7.4. Human $\alpha_2M$ and bovine $\alpha_2M$ were purified on the day of bleeding from fresh acid citrate dextrose plasma by polyethylenglycol precipitation, gel filtration and affinity chromatography as recently described for bovine $\alpha_2M$ (Rantamäki and Müller, 1992). Human IgG and human $\alpha_2M$ converted by trypsin to the fast form, were iodinated by the chloramine T method (Hunter, 1978) to a specific activity of 125 MBq/mg. The preparation of the bovine $\alpha_2M$ peroxidase conjugate ($\alpha_2M$ in the fast form) has recently been described (Rantamäki and Müller, 1992). Goat albumin (Sigma) was conjugated with peroxidase (Boehringer, Mannheim, FRG) in a molar ratio of 1:2 according to Wilson and Nakane (1978). The goat anti rabbit IgG peroxidase conjugate (Bio-Rad, Richmond, Calif., USA) was used for detection of the IgG-binding activity. Bovine serum albumin (fraction V, ria grade) was obtained from USB (cat. no.10868) DNA probes were labelled with alpha$^{32}$P-ATP by a random-priming method (Multiprime DNA labelling system; Amersham Inc, Amersham, England). Nitrocellulose (nc)-filters (Schleicher & Schüll, Dassel, Germany) were used to bind DNA in hybridization experiments or proteins in dot-blot or Western-blot techniques.

In order to analyze protein samples by native or SDS-PAGE the PHAST-system obtained from Pharmacia LKB Biotechnology, Uppsala, Sweden was used according to the suppliers recommmendations.

Routine methods

Methods used routinely in molecular biology are not described such as restriction of DNA with endonucleases, ligation of DNA fragments, plasmid purification etc since these methods can be found in commonly used manuals (Sambrook et al., 1989, Ausubel et al., 1991).

EXAMPLE 1 (A)

Construction and Screening of a Genomic Library From *S. dysgalactiae*, Strain SC1

Chromosomal DNA from *S. dysgalactiae* SC1 was partially digested with Sau3A1, and fragments ranging from 3–8 kb in size were isolated by preparative agarose gel electrophoresis. The DNA fragments were ligated to Lambda GEM-11 BamH1 Arms (Promega, Madison, Wis., USA). After ligation the recombinant molecules were packaged in vitro using the Packagene System (Promega). The resulting phage library was screened for expression of IgG- or $\alpha_2M$-binding activity using $^{125}$I-labelled IgG or $\alpha_2M$, respectively. After generation of plaques on the host strain *E. coli* LE 392, a nc filter (Schleicher & Schüll, Dassel, FRG) was placed on top of the agar plate. The filter was then removed and saturated with 2% BSA in PBS for 1 h at 37° C., rinsed briefly in PBS containing 0.05% Tween 20 (PBS-T).

A second filter treated in the same way was used to obtain a second replica of the plate. The two filters were then incubated with $^{125}$I-labelled $\alpha_2M$ and IgG, respectively, overnight at room temperature in the same buffer. Subsequently the filters were washed 3×15 min in PBS-T, dried and exposed to Kodak XAR5 film for 7 days at −70° C. Plaques that gave a signal with radiolabelled ligands were replaqued and the binding activities verified in a second binding experiment.

EXAMPLE 1(B)

Subcloning and Isolation of Positive Clones

One lambda clone reactive with both ligands, designated A5 was chosen for further studies. The clone was analysed by restriction mapping and a preliminary restriction map was constructed. After HindIII digestion of the phage A5 DNA, fragments were cloned into pUC18. Following transformation, clones were grown overnight on nc filters on agar plates. The nc-filters were replicated to a masterplate and incubated for 10 minutes in chloroform vapour in order to release the proteins from the bacterial cells. After saturation with BSA the filters were incubated with radiolabelled ligands as mentioned above. Positive clones were isolated after 2 days exposure of the filters to Kodak XAR-5 film. One clone, pAM1, reacted with both $\alpha_2M$ and IgG and was selected for further studies. Subcloning of the DNA into a plasmid vector showed that a 2,5 kb HindIII restriction fragment encoded both the $\alpha_2$M and IgG binding.

EXAMPLE 1 (C)

DNA Sequencing and Analysis of the Sequence

The clone pAM 1 was subcloned into pUC18 and pGEM11zf(+)(Promega). The subclones were sequenced by the dideoxy method of Sanger et al.(1977) using "Sequenase, version 2.0" (USB, Cleveland, Ohio, USA). The sequencing samples were analysed on wedge-shaped 6% acrylamide gels containing 7 M urea. The "PC GENE" computer software package (Intelligenetics Inc., Calif., USA) was used for analysis of the DNA sequences.

Sequencing of the HindIII fragment revealed an open reading frame starting with an ATG initiation codon in position 506 and ending with a TAA stop translation codon in position 2498, thus coding for a potential protein of 664 amino acids (Page 31). Preceding the ATG codon, in position 494 to 499, there is a putative ribosome binding site (Page 31, double underlined) similar to those found in other streptococcal genes. Further upstream there are stretches, that constitute possible transcription initiation signals (single underlined). The deduced amino acid sequence of the mig gene contains an N-terminal stretch resembling a secretory signal. There is a possible cleavage point according to the −1, −3 rule (von Heijne, 1986) in amino acid position 30–31. Following the putative signal sequence there is a 178 amino acid stretch containing several repetitive motifs of various length. For example in position 87–110 there is a 24 amino acid stretch, which is repeated once, starting at position 166. The function of the various repeats has so far not been determined. Further downstream the gene is extremely repetitive. In amino acid position 209, starting with alanine, a stretch of 70 amino acids is repeated five times without any intervening segment and with only minor amino acid substitutions within the elements. Downstream these repeats there is a stretch containing many charged amino acids and many prolines, a feature seen in several other streptococcal surface proteins (Fahnestock et al., 1990). This stretch, probably spanning the cell wall, is called W. Further downstream there is a LPTTGE sequence (SEQ ID NO:11) matching the consensus hexapeptide (SEQ ID NO:12) LPXTGX found in all cell wall associated proteins in Gram-positive cocci. In the C-terminal end of the protein there is a hydrophobic stretch ending with a few charged amino acids, constituting the membrane spanning region called M. Further analysis of the nucleotide and amino acid sequence reveals a striking homology between the C-terminal parts of protein MIG and protein G from group G streptococci (Fahnestock et al., 1986; Guss et al., 1986). The five major repeats from protein MIG, responsible for the IgG-binding, comprise amino acid 209 to amino acid 559. The region upstream the initiation codon and also the region encoding the main part of the signal peptide are highly homologous in the two genes (data not shown). The region in the SC1 gene from position 587 to the start of the 70 amino acid repeats (in position 1130) shows no apparent homology to any sequence in the EMBL nucleic acid sequence data bank.

EXAMPLE 1 (D)

Construction of Expression Clones and Purification of Fusion Protein

A protein fusion and purification system (NewEngland Biolabs) was used to construct clones expressing various parts of the mig gene fused to the vector pMalC2. The 1860 bp PvuII-PvuII fragment ranging from position 570 to position 2430 represented the whole gene except the signal sequence and the membrane spanning domain (Page 31 and FIG. 1). This clone was designated pMIG1. The clone containing the 521 bp PvuII-Sau3A fragment from position 570 to 1091 was called pMIG2. Finally the 1104 bp Sau3A-BstNI fragment ranging from position 1091 to 2195 was cloned and the clone was named pMIG3. The different clones were cultivated in 5 liters of LB medium with 50 μg ampicillin/ml, according to the instructions of New England BioLabs. Cells were harvested by centrifugation and subsequently lysed on ice for 30 min in 50 ml lysis buffer, consisting of 10 mM Na$_2$HPO$_4$, 30 mM NaCl, 0.25% Tween 20, 10 mM EDTA, 10 mM EGTA, 1 mM PMSF and 1 mg/ml hen egg white lysozyme (Boehringer Mannheim, FRG). The lysates were then extensively sonicated on ice for 2 min to reduce the viscosity and centrifuged for 30 min at 20 000× g. The clear supernatants were diluted with equal volumes of PBS, containing 0.05% Tween 20 and 0.05% NaN$_3$. The samples were then loaded on an amylose-agarose column (NewEngland BioLabs) at a flow rate of 2 ml/min and after extensive washings with the start buffer the column was eluted with the same buffer, containing 10 mM maltose. Elution was recorded at 280 nm and fractions of 3 ml were collected.

EXAMPLE 1 (E)

SDS-PAGE and Western Blotting

Material from the expression clones was prepared for gel electrophoresis by taking 1 ml of IPTG induced culture, pelleting the cells and resuspending them in sample buffer (Laemmli, 1970) containing SDS and 2-mercaptoethanol. After boiling for 5 min the suspensions were centrifuged in a microfuge and the supernatants applied to the electrophoresis gel in the Mini protean Chamber (Bio-Rad, Richmond, Calif., USA). The samples were separated on a 12,5% acrylamide gel and subsequently stained with Coomassie blue R250 (Serva, Heidelberg, FRG) or blotted onto nc-membranes. The nc-membranes were blocked with 1% BSA in PBS and reacted with peroxidase labelled bovine $\alpha_2$M (Rantamäki and Müller, 1992) and peroxidase labelled goat IgG (Bio-Rad), respectively. After washing with PBST and PBS, the nc membranes were developed with 4-chloro-1-naphthol (Serva) for visualization.

EXAMPLE 1 (F)

Localization of the Different Binding Activities

Figure 2:
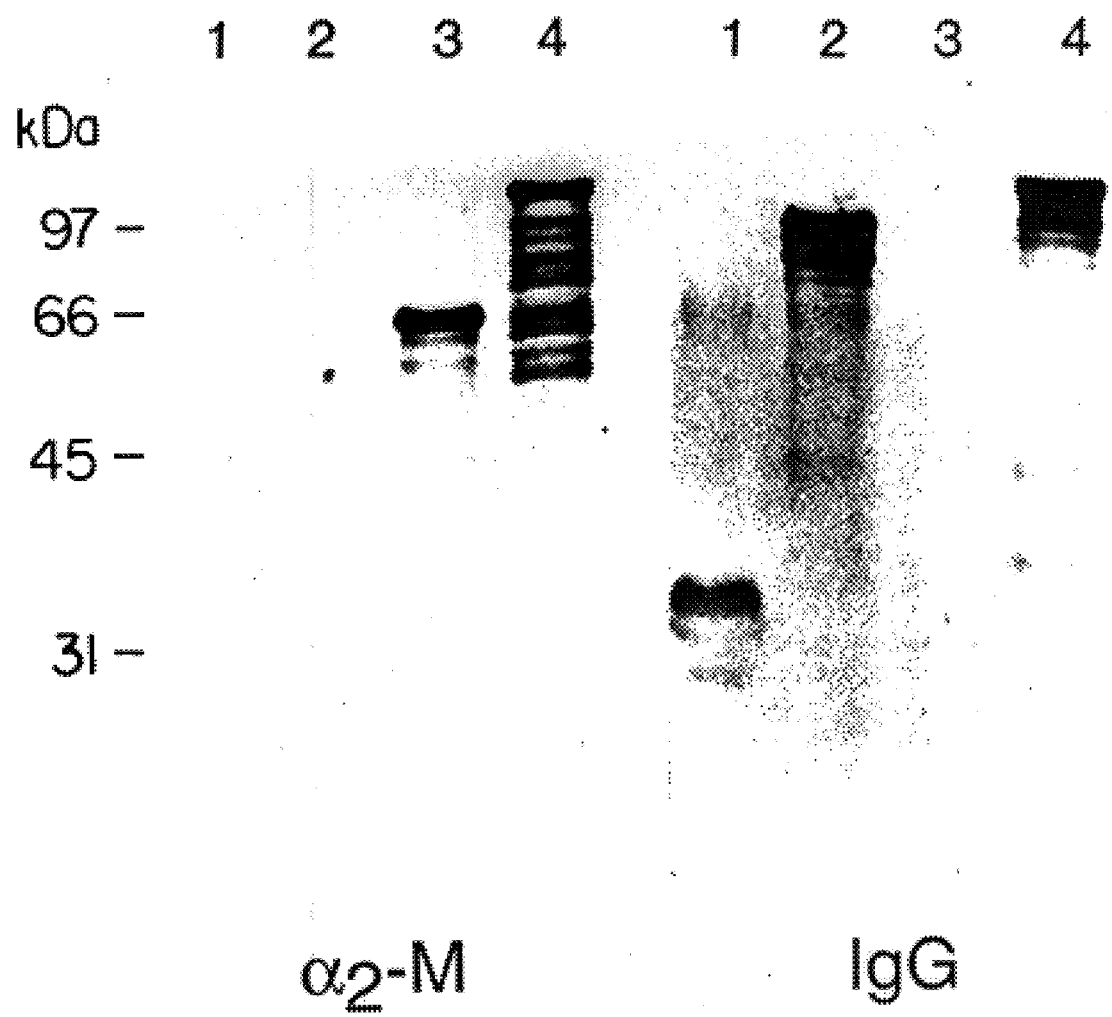
FIG. 2. Western Blot of fusion proteins. The fusion proteins were constructed as indicated in FIG. 2 and produced in *E. coli* strain DH5$\alpha$. Cell lysates were separated by SDS-PAGE, transferred to nitrocellulose and subsequently analyzed for binding activity with $\alpha_2$M (bovine $\alpha_2$M, fast form, peroxidase conjugate) and IgG (goat IgG peroxidase conjugate). Lane 1, recombinant protein G as a control; Lane 2, lysate of clone pMIG3 encoding the 5 IgG-binding regions of protein MIG; Lane 3, lysate of clone pMIG2 encoding the $\alpha_2$M-binding site; and Lane 4, lysate of clone pMIG1 encoding essentially the native protein MIG.
Figure 3A:
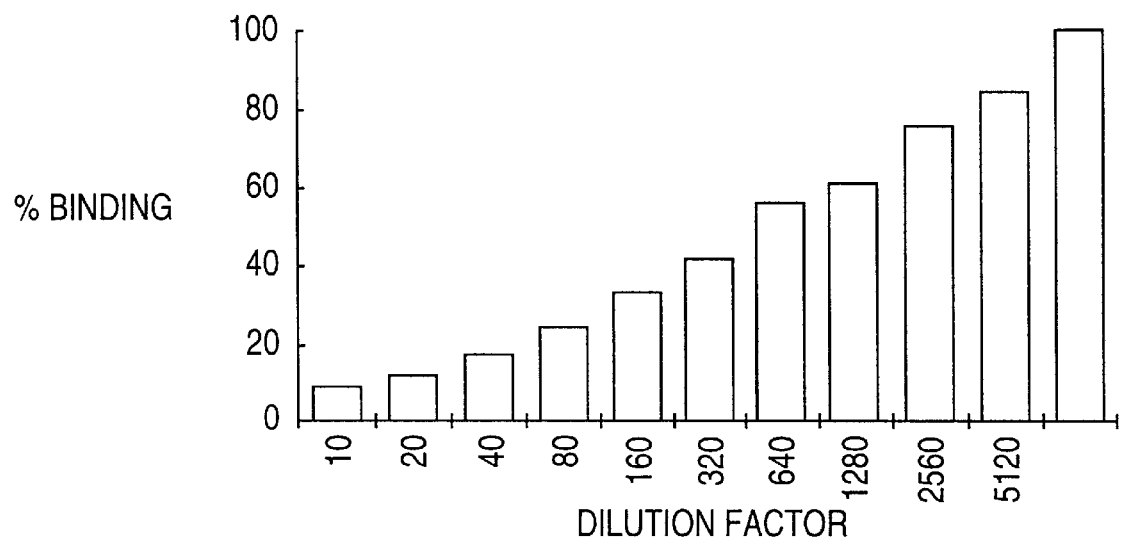
FIGS. 3A–3B. Inhibition of binding of $\alpha_2$M (A) and IgG (B) to *Streptococcus dysgalactiae*, strain SC1 by the fusion proteins encoded by pMIG2 and pMIG3. The purified gene products of pMIG2 and pMIG3 encoding the $\alpha_2$M-binding and IgG-binding domains of protein MIG, respectively, were tested in a microtiter plate inhibition assay. SC1 cells were immobilized on the plates and the binding of labelled ligands was recorded in the presence of increasing amounts of fusion protein. The hatched bar indicates the binding in the absence of fusion protein.
Figure 3B:
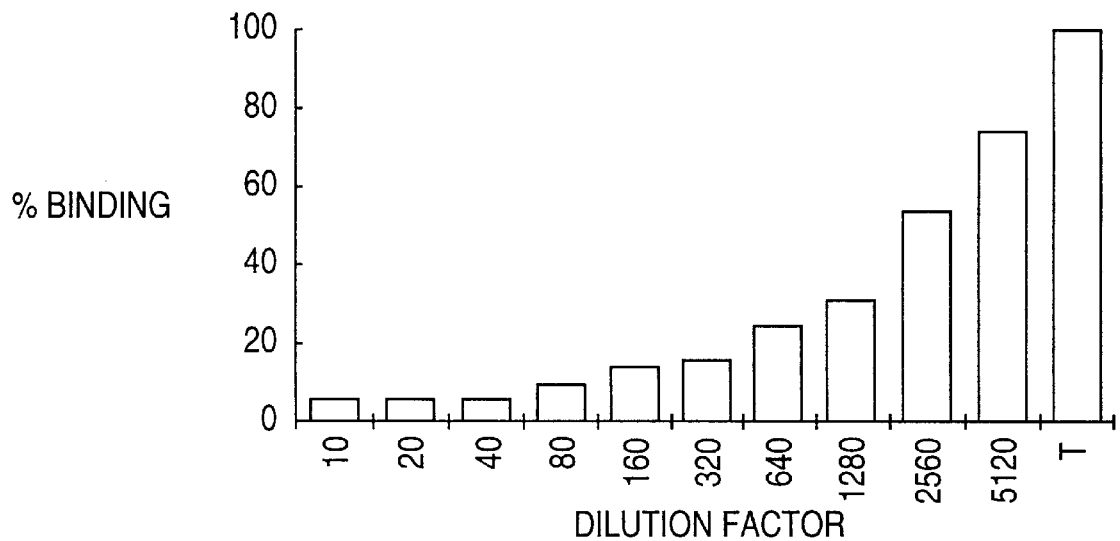

In order to facilitate the purification of the gene products and to determine the location of the two binding activities, a number of expression clones were constructed using the pMAL gene fusion vector (FIG. 1). The reactivity of the different expression clones was tested in Western Blot experiments (FIG. 2). The pMIG1 clone, representing virtually the whole mig gene, bound both $\alpha_2$M and IgG, while the pMIG2 clone, which encoded the unique SC1 sequence upstream to the 70 amino acid repeat region, bound only bovine $\alpha_2$M but neither goat or human IgG nor goat or human albumin. The clone pMIG3, encoding the 5 times repeated 70 amino acid long units, bound only IgG. The two expression clones pMIG2 and pMIG3 were also tested for their ability to inhibit the binding of bovine $\alpha_2$M and goat IgG to their native receptors present on the surface of SC1 cells (FIG. 3). Affinity purified material from the two clones completely inhibited the binding of their corresponding ligand, $\alpha_2$M or IgG, to the streptococcal cells.

EXAMPLE 1 (G)

Inhibition Assay

Flat bottom microtitre plates (Maxisorp, NUNC, Copenhagen, Denmark) were coated with 200 µl of a suspension of guanidinium chloride extracted cells of *S. dysgalactiae*, SC1, as recently described (Rantamäki and Müller, 1992). To demonstrate inhibition of bovine $\alpha_2$M-binding to the immobilised SC1 cells by the recombinant $\alpha_2$M-R, 2-fold serial dilutions of the purified fusion protein encoded by pMIG2 were applied to the wells in aliquots of 100 µl and to each well 100 µl of peroxidase labelled bovine $\alpha_2$M in a predilution of 1:4000 was added. For demonstration of the inhibitory activity of the recombinant FC-R, the fusion protein encoded by pMIG3 was 2 fold serially diluted and 100 µl of each dilution step applied per well. One hundred µl of the peroxidase labelled goat anti rabbit-IgG (BioRad) in a dilution of 1:4000 were then mixed with the fusion protein and the plate allowed to stand for 4 h at room temperature. The plate was subsequently washed 5 times with PBS-T and developed using 3,3',5,5',-tetramethyl benzidine (Boehringer) as substrate (Bos et al., 981). Finally the developed blue colour was converted to yellow by addition of 100 µl 1M $H_2SO_4$ and the plate was read at 450 nm in an ELISA reader (BIOTEK). The result is shown in FIG. 3.

EXAMPLE 2 (A)

Isolation of a Lambda Clone Originating from *S. dysgalactiae* Strain 8215 Which Codes for Polypeptides Possessing $\alpha_2$M-, BSA-, and IgG-binding Activity A gene library for *S. dysgalactiae* strain 8215 was produced in a manner analogous to that described by Frischauf et al. (1983).

Streptococcal DNA was partially digested with Sau3A1 and ligated into BamHI-cleaved lambda EMBL3 vector arms. The ligated DNA was packaged in vitro into phage particles which were then allowed to infect *E. coli* P2392 cells. The resultant phage library was analysed for $\alpha_2$M-, BSA- and IgG-binding activity. The resultant phage library was analysed for this purpose on agar plates in soft agar layer which were incubated overnight at 37° C. The next day plates having a plaque frequence of $10^3$–$10^4$ were selected. The plaques from each plate were transferred by replica plating to nc-filters. Transfer was allowed to proceed at room temperature for about 15 min. The filters were subsequently removed and soaked, using gentle agitation., for 30 min in a PBS-T solution (250 ml/10 filter with three changes of the PBS-T solution in order toremove loosely bound material such as cell debris and components from the growth media). The filters were then sorted into three groups where replicas originating from the same agarplate were represented in each grou. The respective group of filters were transferred to a petri dish which either contained approximately $10^7$ cpm of $^{125}$I-labelled rabbit-IgG-antibodies (specific actiivity 7 mCi/mg) in PBS-T, approximately $10^7$ cpm of $^{125}$I-labelled BSA (specific activity 7 mCi/mg) or approximately $10^7$ cpm of $^{125}$I-labelled f$\alpha_2$M (specific activity 125 MBq/ml). After incubation for 2 h at room temperature using gentle agitation the respective group of filters were washed separately for 3×10 min in 250 ml PBS-T at room temperature (this washing procedure is important to reduce background signals and have to be prolonged if necessary). After washing the filters were dried and autoradiographed for several days. Analysis of the autoradiogram revealed several plaques reacting with the three labelled ($\alpha_2$M,IgG and BSA) ligands. By comparing autoradiograms corresponding to the different ligands clones binding all three ligands were selected on the original agar plate and replaqued and the binding activities verified in an another round of binding assays as described above. Finally one clone called "lambda SD1" expressing all three activities was chosen for the subsequent procedures. The use in biotechnology of the serum albumin binding properties of protein MAG are described in a copending patent application entitled "Method and Means for Producing Plasmaprotein-binding Proteins" filed Sep. 6, 1993 (Nr. 9302856-1).

EXAMPLE 2 (B)

Characterization of the Lambda SD1 Clone

Purified phage DNA from the lambda SD1 clone was analysed by restriction mapping and a preliminary restriction map was constructed. After HindIII digestion of the lambda SD1 DNA, fragments were cloned into the pGEM11Zf(+) previously cleaved with HindIII. After ligation and transformation into *E. coli* strain DH5α recombinant clones were screened for expression of $\alpha_2$M-, BSA- and/or IgG-binding activity. This was done as follows: Clones were grown over night on nc-filters on agar plates. Next day the nc-filters were replica plated to a masterplate whereupon the filters were incubated for 10 min in chloroform vapour in order to release the proteins from the bacterial cells. After washing the filters in large excess of PBS-T (in this step it is important to reduce the bacterial debris attached to the filter to avoid unspecific binding of the labelled ligands used in the next step thereby reducing the background signals) the filters were transferred to petri dishes containing $^{125}$I-labelled $\alpha_2$M, BSA, or IgG, respectively as in Example 2A above. After incubation for 2 h at room temperature under gentle agitation the filters were washed in PBS-T, dried and autoradiographed as mentioned in Example 2A. After 2 days of exposure of the filters the autoradiograms were analysed and clones expressing $\alpha_2$M-binding activity were isolated. One such clone called pSD100 harbouring an aproximately 0,9 kb HindIII insert was chosen for further studies. Clones expressing BSA-or IgG-binding activity could not be identified. In order to identify clones encoding the BSA and IgG-binding activity, a $^{32}$P labelled DNA (random-priming) probe homologous to the domain encoding the IgG-binding regions of protein G (Guss et al., 1986) was used to identify the presence of homologous sequences among the recombinant plasmid clones. Among several HindIII clones hybridizing to this probe one called pSD101 containing an approximately 0,7 kb insert was selected for further studies.

EXAMPLE 2 (C)

Sequence Analysis of the mag Gene

The nucleotide (nt) sequences of the HindIII inserts of pSD100 and pSD101 were determined and the nt and deduced amino acid (aa) sequences were compared with the corresponding sequences from earlier published sequences of type III Fc receptors (Fahnestock et al., 1986, Guss et al., 1986, Olsson et al., 1987). This analysis revealed only short stretches of homology within the 862 bp HindIII insert of pSD100 to the other type III Fc receptor genes while the 693 bp HindIII insert of pSD101 was highly homologous to the earlier studied receptor genes. The combined size of the directly linked inserts of pSD100 and pSD101 containing the whole gene, called mag, is 1555 nt (FIG. 4). There is a potential ATG start codon at nt position 288 preceded by a nt sequence resembling a ribosome-binding site. Upstream this site there are several potential promoter sequences. Starting at the ATG codon there is an open reading frame of 1239 nt terminating in a TAA stop codon at nt 1527. Thus the gene encodes a 413 aa protein, termed protein MAG, with a calculated molecular mass of approximately 44 kDa including a putative signal peptide. The N-terminal part of the protein, constituting the signal peptide, shows a high degree of homology to the corresponding domains of the other type III receptors. A possible signal peptidase cleavage site should be after the alanine residue at aa position 34 in FIG. 4.. Downstream the signal peptide there is a unique strech of 158 aa. No repeated motifs can be seen in this part of the protein from strain 8215. Further to the C-terminal end the deduced aa sequence starting with -ALK- in position 193–195 shows homology to parts of the albumin-binding domain of protein G, the type III Fc receptor from the group G streptococcal strain G148 (Björck et al., 1987, Nygren et al., 1988). In the 8215 receptor this part is only 50 aa long and is directly followed by a region, which is highly homologous to the IgG-binding domains found in other type III Fc receptors. Also in the C-terminal part of the protein, which is responsible for anchorage of the protein to the bacterial cell surface, there is a striking sequence homology to other cell wall associated streptococcal proteins. This part of the protein can be divided into two structural and functional different domains. The N-terminal part, called W, (FIG. 4) is extremely hydrophilic and consists of mainly charged residues and prolines. This part of the protein probably mediates the attachment to the cell wall. Following the W-region, there is a hexapeptide (SEQ ID NO:11) LPTTGE, matching the consensus sequence (SEQ ID NO:12) LPXTGX commonly found in wall achored surface proteins of Gram-positive cocci (FIG. 4). Downstream this motif there is a region of hydrophobic residues, called M, spanning the cell membrane, followed by a stretch of positively charged residues in the C-terminal end of the protein.

EXAMPLE 2 (D)

Localization of Binding Domains in Protein MAG

Figure 5B:
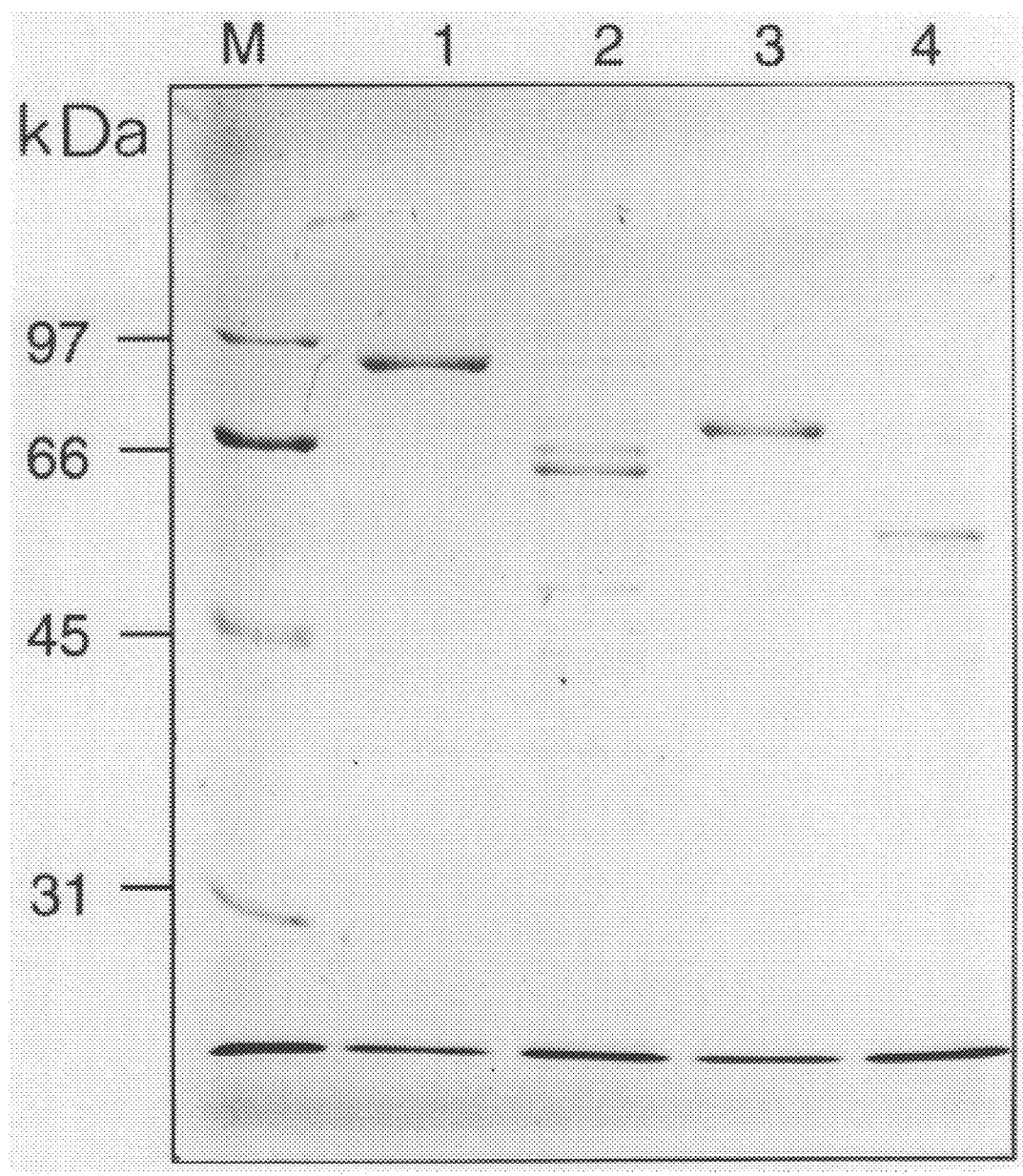

On the basis of the sequence analysis we used a fusion protein expression system (obtained from Biolabs) to produce the various domains of protein NAG (FIG. 5A). The high homology between the 3' end of the gene and the genes of earlier described type III Fc receptors strongly suggested that this part of the sequence is encoding the IgG-binding activity. In Western-blot experiments we could show that this was indeed the case (see legends to FIGS. 5A, B and C). The fusion protein encoded by the construct pMAG3 showed no reactivity with $\alpha_2M$ but a strong signal was obtained with labelled albumin and IgG (FIGS. 5B and C). This construct encodes an IgG-binding domain and also the 50 aa sequence upstream that domain which is partially homologous to the albumin-binding domains of protein G (Björck et al., 1987, Nygren et al., 1988). The subclone pMAG4, encoding the same 50 aa and 10 aa from the IgG-binding domain, was reactive with albumin but not with IgG or $f\alpha_2M$ (FIGS. 5B and C). In addition, the subclone pMAG2, encoding the unique 158 aa long stretch in the N-terminal part of the protein reacted only with $\alpha_2M$. Expression of the clone pMAG1, (representing the whole gene), bound all three ligands.

EXAMPLE 2 (E)

Schematic Presentation of the Construction of the Expression Clones pMAG1–4 pMAG1: lambda SD1 was cleaved with PvuII. The approximately 1.1 kb PvuII fragment representing almost the complete mag gene was purified using preparative agarose gel-electrophoresis and ligated into the vector pMALC2 (the vector had previously been cleaved with EcoRI and the sticky ends converted to blunt ends using T4 DNA polymerase.

pMAG2: the 870 bp HindIII fragment from pSD100 was purified by preparative agarose gel-electrophoresis. The purified HindIII-fragment was cleaved by PvuII and a part of the cleaved material was subsequently ligated into the pMALC2 vector (the vector had earlier been cleaved with EcoRI and the generated sticky ends converted to blunt ends using T4 DNA polymerase. After inactivation of the T4 DNA polymerase the vector was cleaved with HindIII).

pMAG3: the 670 bp HindIII fragment from pSD101 was purified by preparative agarose gel-electrophoresis. The purified fragment was cleaved with PvuII and made blunt end with T4 DNA polymerase. The cleaved material was ligated into pMALC2 (the vector had previously been cleaved with EcoRI and BamHI and the sticky ends converted to blunt ends using T4 DNA polymerase.

pMAG4: the 670 bp HindIII fragment from pSD101 was purified using by preparative gel-electrophoresis. The purified fragment was cleaved with HgaI and the sticky ends converted to blunt ends using T4 DNA polymerase and ligated into the pMALC2 vector (the vector had earlier been cleaved with EcoRI and BamHI and converted to blunt ends using T4 DNA polymerase. After ligation and transformation into E.coli DH5α the generated clones were screened for binding activities as described above. Clones expressing various binding activities were identified and called pMAG1–4. The presence of the expected inserts in pMAG1–4 were verified by nt sequencing (including nt sequencing over the junctions between vector and insert).

EXAMPLE 2 (F)

Purification of Protein MAG Using the Lambda SD1 Clone

The lambda SD1 phages were allowed to adsorb to E. coli P2392 cells in 3 individual tubes containing each 3 ml of an overnight culture (37° C., LB-medium with 0.2% maltose and 10 mM $MgCl_2$) at a m.o.i. of ~0,2 for 15 min at 37° C. After adsorption, the phage/bacteria solutions were transferred to three E-flasks each containing 500 ml LB-medium prewarmed to 37° C. The E-flasks were shaken vigorously at 37° C. until lysis occured. Then 2 ml of chloroform was added to the respective flasks and the flasks shaken for additional 10 min. The lysed cultures were subsequently centrifugated at ~15000 g for 40 min and the respective supernatants removed pooled and filtered (0,45 μm nc-filters, Schleicher & Schüll). The filtered media were passed over a column containing IgG-Sepharose 6FF (3 ml sedimented gel which had previously been washed with PBS, pre-eluted with 1 M HAc pH 2,8, washed and equilibrated with PBS). The column was sequencially washed with 30 ml PBS, 60 ml PBS-T and 30 ml distilled $H_2O$. The bound protein material was eluted with 12 ml 1 M HAc pH 2,8. The eluted fraction was lyophilized and the dried material was dissolved in a TE-buffer (10 ml Tris/HCl pH 7,5; 1 mM EDTA). SDS-PAGE analysis (a 8–25% gradient gel run under reducing conditions in the PHAST-system and then stained with Coomassie-blue) showed that the affinity purified material was of high yield and homogeneous in size with a band having the relative migration corresponding to a protein of ~45 kDa (using the low molecular weight marker kit obtained from Bio-Rad). Thus the above described system is well suited to obtain protein MAG. The protein MAG produced in this way had when tested separately all three binding activities (f$\alpha_2$M-, albumin- and IgG-binding activities).

EXAMPLE 3 (A)

Isolation of a Lambda Clone Originating From *S. equi* supsp *zooepidemicus* strain V Which Codes for Polypeptides Possessing $\alpha_2$M- and IgG-binding Activities A gene library for *S. equi* supsp. *zooepidemicus* strain V was produced in a manner analogous to that described by Frischauf et al., (1983).

Streptococcal DNA was partially digested with Sau3A1 and ligated into BamHI-cleaved lambda EMBL3 vector arms. The ligated DNA was packaged in vitro into phage particles which were then allowed to infect *E. coli* P2392 cells. The resultant phage library was analysed for $\alpha_2$M- and IgG-binding activity. The resultant phage library was analysed for this purpose on agar plates in soft agar layer which were incubated overnight at 37° C. The next day plates having a plaque frequence of $10^3$–$10^4$ were selected. The plaques from each plate were transferred by replica plating to nc-filters. Transfer was allowed to proceed at room temperature for about 20 min. The filters were subsequently removed and soaked, using gentle agitation, for 30 min in a PBS-T solution (250 ml/10 filters with 3 changes of the PBS-T solution in order to remove loosely bound material such as cell debris and components from the growth media). The filters were then sorted into two groups where replicas originating from the same agarplate were represented in each group. The respective group of filters were transferred to a petri dish which either contained approximately $10^7$ cpm of $^{125}$I-labeled rabbit-IgG-antibodies (specific activity 7 mCi/mg) in PBS-T or approximately $10^7$ cpm of $^{125}$I-labelled HSA (specific activity 7 mCi/mg) or approximately $10^7$ cpm of $^{125}$I-labelled f$\alpha_2$M. After incubation for 2 h at room temperature using gentle agitation the respective group of filters were washed separately for 3x10 min in 250 ml PBS-T at room temperature (this washing procedure is important to reduce background signals and has to be prolonged if necessary). After washing the filters were dried and autoradiographed for several days. Analysis of the autoradiogram revealed several plaques reacting with the labelled ligands ($\alpha_2$M,IgG and HSA). By comparing autoradiograms corresponding to the different ligands clones binding all three ligands were selected on the original agar plate and replaqued and the binding activties verified in an another two round of binding assay as described above. Finally one clone called "lambda SZG1" expressing all three activities was chosen for the subsequent procedures.

EXAMPLE 3 (B)

Characterization of the Lambda SZG1 Clone

Purfied phage DNA from the lambda SZG1 clone was analysed by restriction mapping and a preliminary restriction map was constructed. After EcoRI digestion of the lambda SZG1 DNA, fragments were cloned into the pUC19 vector previously cleaved with EcoRI. After ligation and transformation into *E. coli* strain DH5$\alpha$ recombinant clones were screened for expression of f$\alpha_2$M-, and/or IgG-binding activity. This was done as follows clones were grown over night on nc-filters on agar plates. Next day the nc-filters were replica plated to a masterplate whereupon the filters were incubated for 10 min in chloroform vapour in order to release the proteins from the bacterial cells. After washing the filters in large excess of PBS-T (in this step it is important to reduce the bacterial debris attached to the filter to avoid unspecific binding of the labelled ligands used in the next step thereby reducing the background signals) the filters were transferred to petri dishes containing $^{125}$I-labelled f$\alpha_2$M or IgG, respectively as in Example 2 (A) above. After 2h incubation at room temperature under gentle agitation the filters were washed in PBS-T, dried and autoradiographed as mentioned in Example 2 (A). After 2 days of exposure of the filters the autoradiograms were analysed and clones expressing both f$\alpha_2$M-, and IgG-binding activity were isolated. One such clone called pSZG40 harbouring a approximately 2,9 kb EcoRI insert was chosen for further studies.

EXAMPLE 3 (C)

Sequence Analysis of the Insert of pSZG40 Containing the zag Gene

The nucleotide (nt) sequences of the ~2.9 kb EcoRI inserts of pSZG40 was determined and the nt and deduced amino acid (aa) sequences were compared with earlier published sequences of type III Fc receptor genes (Fahnestock et al., 1986, Guss et al., 1986, Olsson et al., 1987) and the sequences of the mig and mag genes. This analysis revealed stretches in the zag gene homologous to the other mentioned genes. The protein encoded by the zag gene is termed protein ZAG.

EXAMPLE 3 (D)

Localization of the f$\alpha_2$-binding Domain in Protein ZAG

On the basis of the sequence analysis we used a fusion protein expression system (obtained from Biolabs) to produce various domains of protein ZAG. The 2,9 kb fragment from pSZG40 was purified by preparative agarose gel electrophoresis. The purified fragment was further digested with XmnI and HhaI. After digestion the cleavage mixture was separated on a second preparative agarose gel and a ~500 bp XmnI/HhaI fragment was isolated. The ends of the isolated fragment were converted to blunt ends using T4 DNA polymerase and the fragment was subsequently ligated into pMALC2 (previously cleaved with XmnI). After transformation a clone expressing $\alpha_2$M-binding was isolated. This clone was called pZAG2. The insert of pZAG2 is shown in FIG. 6. Another clone pZAG3 harbouring a ~500 bp HhaI/HincII fragment encoding the IgG-binding activity was constructed in the following way. The ~2,9 kb EcoRI fragment mentioned above, was cleaved with HhaI and HincII and the cleavage mixture separated on a preparative agarose gel. The ~500 bp HhaI/HincII fragment was isolated, converted to blunt end with T4 DNA polymerase and cloned into pMALC2 previously cleaved with XmnI. The pZAG3 clone express IgG-binding activity but not f$\alpha_2$M-binding activity.

EXAMPLE 3 (E)

Purification of Protein ZAG Using the Lambda SZG1 Clone

The lambda SZG1 phages were allowed to adsorb to cells of 3 individual tubes containing 3 ml *E. coli* P2392 (from an over night culture grown at 37° C. in LB-medium with 0.2% maltose and 10 mM MgCl$_2$) at a m.o.i. of ~0,2 for 15 min at 37° C. After adsorption, the phage/bacteria solutions were transferred to three E-flasks each containing 500 ml LB-medium prewarmed to 37° C. The E-flasks were shaken vigorously at 37° C. until lysis occured. Then 2 ml of chloroform was added to the respective flasks and the flasks shaken for additional 10 min. The lysed cultures were subsequently centrifugated at ~15000 g for 40 min and the respective supernatants removed pooled and filtered (0,45 um nc-filters, Schleicher & Schüll). The filtered media was passed over a column containing IgG-Sepharose 6FF (3 ml sedimented gel which had previously been washed with PBS, preeluted with 1 M HAc pH 2,8, washed and equilibrated with PBS. The column was sequencially washed with 30 ml PBS, 60 ml PBS-T and 30 ml distilled H$_2$O. The bound protein material was eluted with 12 ml 1 M HAc pH 2,8. The eluted fraction was lyophilized and the dried material was dissolved in a TE-buffer (10 ml Tris/HCl pH 7,5; 1 mM EDTA). SDS-PAGE analysis (a 8–25% gradient-gel run under reducing conditions which was subsequently stained with Coomassie-blue) showed that the affinity purified material was of high yield and homogeneous in size with a band having the relative migration corresponding to a protein of ~45 kDa (using the low molecular weight marker kit obtained from Bio-Rad). Thus the above described system is well suited to obtain protein ZAG.

Conclusions

The binding of the fast form of $\alpha_2$M to the MIG, MAG and ZAG proteins is mediated by novel sequences extending N-terminally from the IgG-binding domains of the respective proteins. Although large parts of these sequences are dissimilar, cross-inhibition assays have revealed that the $\alpha_2$M-binding regions of the proteins MIG, MAG and ZAG interact with the same or closely to each other located domains of the $\alpha_2$M molecule. The IgG-binding domains alone, produced as fusion proteins, did not show any reactivity with f$\alpha_2$M. The highly homologous recombinant protein G used in control experiments similarly did not react with the $\alpha_2$M but only with the IgG. Thus, the only binding activity of the ~70 amino acid IgG-binding segments in protein MIG, MAG and ZAG and the corresponding segments in protein G from strain G148 is the binding of IgG. These results argue against earlier data published by Sjöbring et al. (1989), that the IgG domains of protein G also bind $\alpha_2$M.

After the submission of the first patent application on the Sep. 6, 1993 (Nr. 9302855-3, the priority claim), more extended data of the three $\alpha_2$M-binding proteins described above (see examples 1–3) have been published. For a detailed description of the protein MIG and its gene see reference Jonsson and Müller, 1994, for protein MAG the key reference is Jonsson et al., 1994. The protein ZAG and its gene as well as a comparison of all 3 $\alpha_2$M-binding proteins have been described in the thesis of Hans Jonsson: "Cell surface proteins of animal group G streptococci mediating binding to plasma proteins", Uppsala 1994.

REFERENCES

Ausubel, F. A., Brent, R., Kingston, R. E., Moore, D. D., Seidman, J. G., Smith, J. A. and Struhl. K. (eds) (1991) *Current Protocols in Molecular Biology,* Greene Publishing and Wiley-Intersciences, New York.

Barrett, A. J., Brown, M. A. and Sayers, C. A. (1979) The electrophoretically slow and fast forms of the $\alpha_2$-macroglobulin molecule. *Biochemical Journal* 181, 401–418.

Björck, L., Kastern, W., Lindahl, G and Wideback, K. (1987) Streptococcal protein G, expressed by streptococci or by *Escherichia coli* has separate binding sites for human albumin and IgG. *Mol. Immunol.* 24, 1113–1122.

Björck, L. and Åkerström, B. (1990) Streptococcal protein G. In *Bacterial Immunoglobulin-binding proteins.* Boyle, M. P. D. (ed) Academic Press Inc. CA, USA. 1, 113–126.

Bos, E. S., Van Der Doelen, A. A., Van Rooy, N. and Schuurs, A. H. W. M. (1981) *Journal of Immunoassays* 2, 187–204.

Fahnestock, S. R., Alexander, P., Nagle, J. and Filipula, D. (1986) Gene for an immunoglobulin-binding protein from a group G streptococcus. *J. Bacteriol.* 167, 870–880.

Guss, B., Eliasson, M., Olsson, A., Uhlen, M., Frej, A.-K., Jörnvall, H., Flock, J.-I. and Lindberg, M. (1986) Structure of the IgG-binding regions of streptococcal protein G. *EMBO J.* 5, 1567–1575.

Justus, C. W. E., Müller, H.-P., Simon, M. M. and Kramer, M. D. 1990 Quantification of free $\alpha_2$-macroglobulin and $\alpha_2$-macroglobulin-protease complexes by a novel ELISA system based On streptococcal $\alpha_2$-macroglobulin receptors. *Journal of Immunological Methods* 126 103–108

Frischauf, A.-M., Lehrach, H., Poustka; A. and Murray, N. (1983) Lambda replacement vectors carrying polylinker sequences. J. Mol. Biol. 170, 827–842.

Hunter, W. M. (1978) In *Handbook of experimental immunology* (Weir, D. M., ed.), pp 14.1–14.40, Blackwell Scientific, Oxford.

Jonsson, H. and Müller, H.-P. (1994) The type III Fc receptor from *Streptococcus dysgalactiae* is also an $\alpha_2$-macroglobulin receptor. *Eur. J. Biochem.* 220, 819–826.

Jonsson, H., Frykberg, L., Rantamäki, L. and Guss, B. (1994) Mag, a novel plasma protein receptor from *Streptococcus dysgalactiae. Gene* 143, 85–89.

Jonsson, H. (1994) Cell surface proteins of animal group C streptococci mediating binding of plasma proteins. Dissertation, Swedish University of Agricultural Sciences, Uppsala, Sweden (ISBN 91-576-4831-X).

Laemmli, U. K. (1970) Cleavage of structural proteins during the assembly of the head of bacteriophage T4. *Nature* 227, 680–685.

Müller, H.-P. and Blobel, H. (1983a) Purification and properties of a receptor for the Fc-component of immunoglobulin G from *Streptococcus dysgalactiae. Zbl. Bakt. Hyg., Abt. Orig. A* 254, 352–360.

Müller, H.-P. and Blobel, H. (1983b) Absorption of human $\alpha_2$-macroglobulin with selected strains of streptococci. *Med. Microbiol. Immunol.* 172, 33–39.

Müller, H.-P. and Blobel, H. (1985) Binding of human $\alpha_2$-macroglobulin to streptococci of group A, B, C, and G. In *Recent advances in streptococci and streptococcal diseases* (Kimura, Y., Kotami, S. and Shiokawa, S., eds) pp 96–97, Reedbooks Ltd., Chertsey.

Nygren, P.-Å., Eliasson, M. Palmcrantz, E., Abrahmsen, L. and Uhlèn, M. (1988) Analysis and use of the serum albumin binding domains of streptococcal protein G. *J. Mol. Recognit.* 1, 60–74.

Nygren, P.-Å., Flodby,, P. Andersson, R., Wigzell, H. and Uhlén, M. (1991) In vivo stabilization of a human recombinant CD4 derivative by fusion to a serum albumin-binding receptor. *Vaccines 91, Modern approaches to vaccine development.* Chanock, R. M. et al. (eds) Cold Spring Harbor Laboratory Press, New York. USA 363–368.

Nygren, P.-Å., Ljungquist, C., Trömborg, H., Nustad, K. and Uhlen, M.(1990) Species-dependent binding of serum albumins to the streptococcal receptor protein G. *Eur. J. Biochem.* 193, 143–148.

Olsson, A., Eliasson, M., Guss, B., Nilsson, B., Hellman, U., Lindberg, M. and Uhlen, M. (1987) Structure and evolution of the repetitive gene encoding streptococcal protein G. *J. Eur. Chem.* 168, 319–324.

Raeder, R., Otten, R. A. and Boyle, M. D. P. (1991) Comparison of albumin receptors expressed on bovine and human group G streptococci. *Infect. Immun.* 59, 609–616.

Rantamäki, L. K. and Müller, H.-P. (1992). Isolation and characterization of $\alpha_2$-macroglobulin from mastitis milk. *J. Dairy Res.* 59, 273–285.

Sambrook, J., Fritsh, E. F. and Maniatis, T. (1989) *Molecular cloning, A laboratory manual,* second ed. Cold Spring Harbour Laboratory Press, New York.

Sanger, F., Nicklen, S. and Coulson, A. R. (1977) DNA sequencing with chain-terminating inhibitors. *Proc. Natl. Acad. Sci. USA* 74, 5463–5467.

Sjöbring, U. (1992) Isolation and molecular characterization of a novel albumin-binding protein from group G streptococci. *Infect. Immun.* 60, 3601–3608.

Sjöbring, U., Falkenberg, C., Nielsen, E., Akerström, B. and Björck, L. (1988) Isolation and characterization of a 14-kDa albumin-binding fragment of streptococcal protein G. *J. Immunol.* 140, 1595–1599.

Sjöbring, U., Trojnar, J., Grubb, A., Åkerström, B. and Björck, L. (1989) Ig-binding bacterial proteins also bind proteinase inhibitors. *J. Immunol.* 143, 2948–2954.

Sjöbring, U., Björck, L. and Kastern, W. (1989) Protein G genes: structure and distribution of IgG-binding and albumin-binding domains. *Mol. Immunol.* 3, 319–327.

Sjöbring, U., Björck, L. and Kastern, W (1991) Streptococcal protein G: gene structure and protein binding properties. *J. Biol. Chem.* 266, 399–405.

Ståhl, S., Sjölander, A., Nygren, P.-Å., Berzins, K., Perlmann, P. and Uhlèn, M. (1989) A dual expression system for the generation, analysis and purification of antibodies to a repeated sequence of the Plasmodium falciparum antigen Pf155/RESA. *J. Immunol. Meth.* 124, 43–52.

Wideback, K. (1987) Binding of albumin fragments to surface receptor in A, C and G streptococci. *Acta path. immmunol. scand. Sect B* 95, 303–307.

Wideback, K., Havlicek, J. and Kronvall, G. (1983) Demonstration of a receptor for mouse and human serum albumin in Streptococcus pyogenes. *Acta path. microbiol. inmunol. scand. Sect B.* 91, 373–382.

Wideback, K. and Kronvall, G. (1987) Isolation of a specific albumin receptor from a group G streptococcal strain. *Acta path. microbiol. immunol. scand. Sect B.* 95, 203–210.

Wilson, M. B. and Nakane, P. K. (1978) Recent developments in periodate method of conjugating horseradish peroxidase (HPRO) to antibodies. In *Immunofluorescence and related staining techniques* (Knapp, W., Holubar, K. and Wick, G., eds), pp 215–224, Elsevier, Amsterdam.

Von Heijne, G. (1986) A new method for predicting signal sequence cleavage sites. *Nucleic Acids Res.* 14, 4683–4690.

Akerström, B., Nielsen, E. and Björck, L. (1987) Definition of IgG- and albumin binding regions of streptococcal protein G, *J. Biol. Chem.* 262, 13388–13391.

Patents or patent applications cited;

WO 84/03103

U.S. Pat. No. 4,237,224

---

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
        (A) LENGTH: 2526 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 506..2497

(ix) FEATURE:
        (A) NAME/KEY: mat_peptide
        (B) LOCATION: 506..2497

(xi) SEQUENCE DESCRIPTION: SEQ ID NO:1:

```
AAGCTTCACA GGTATTTCAC CAGTAGATGC TTTTTGTGGT CTTATTGACA CGCACTTGTG      60

GCGAGAGTAC TGAAACTAAA GCGAAAAACG AACTACTATA AAAGAATAT TAGTCAAGCG      120

TTGGGAGATA TTCTCCTAAC GTTTTTTTGA CAAAAAATGA TTGATCTCTG TTACGAAATA     180

AATAAACGGT GATATTGACA GAAAATCCCA TTTTTATAAA ACTTTATTTT ATTATAAAAG     240
```

-continued

```
AAAGTAATTT TTGAAAAATT ATAGAAAACC ACTTTTATGC TAATAAAATA GCCATAAATA      300

TAAATTGATG AGTCTATGAT AGGAGATTTA TTTGCCAGGA TTTCCTAATT TTATTAATTT      360

AACGAAAATT GATAGAAAAA TTAAATGAAA TCCTTGATTT AATTTTGTTA AGTTGTATAA      420

TAAAAGGTGA AATTATTAGA TTGTAGTTTC AAATTTTTTG GTTTTTTAAT ATGTGCTGGC      480

GTATTAAATA AAAAGGAGA AAGTA ATG GAA AAA GAA AAA AAA GTA AAA TAC         532
                           Met Glu Lys Glu Lys Lys Val Lys Tyr
                            1               5

TTT TTA CGT AAA TCA GCT TTT GGA TTA GCG TCT GTA TCA GCT GCG TTT        580
Phe Leu Arg Lys Ser Ala Phe Gly Leu Ala Ser Val Ser Ala Ala Phe
 10              15                  20                  25

TTA GTT TCG GGA GCA CTA GAA AAT ACT ATA ACT GTT TCT GCA GAA ACT        628
Leu Val Ser Gly Ala Leu Glu Asn Thr Ile Thr Val Ser Ala Glu Thr
                 30                  35                  40

ATA CCT GCA GCG GTC ATT GTA CCT GTT GGC CTA GAT ACT ACA GAA TTA        676
Ile Pro Ala Ala Val Ile Val Pro Val Gly Leu Asp Thr Thr Glu Leu
                 45                  50                  55

CAA AAA TGG TAT GAC ATT GCA AAT GAT TTA GTT GCG ACT GAC AAT GCT        724
Gln Lys Trp Tyr Asp Ile Ala Asn Asp Leu Val Ala Thr Asp Asn Ala
         60                  65                  70

ACT CCG GGA GGC GTA TTT ACA GCA GAC TCA ATG AAG GCA TTA TAT CGT        772
Thr Pro Gly Gly Val Phe Thr Ala Asp Ser Met Lys Ala Leu Tyr Arg
         75                  80                  85

TTA CTA AAT GAT GCA TAC GAT GTG TTG GAA TCA AAA GAC TAT AGA AAA        820
Leu Leu Asn Asp Ala Tyr Asp Val Leu Glu Ser Lys Asp Tyr Arg Lys
 90                  95                 100                 105

TAT GAT TCT CAA GAT AGG ATT GTT GAA TTG GTA AAC AAT TTA AAG AAT        868
Tyr Asp Ser Gln Asp Arg Ile Val Glu Leu Val Asn Asn Leu Lys Asn
                110                 115                 120

ACT ACG CAG TCT CTT TTA CCA ATT GGA GTA GAA CCA GTA GTA TTT GAT        916
Thr Thr Gln Ser Leu Leu Pro Ile Gly Val Glu Pro Val Val Phe Asp
                125                 130                 135

ACT ACT CGC TTG AAT ACC TGG TAT GAT GCT GCT AAT GAA ATT GTT AAT        964
Thr Thr Arg Leu Asn Thr Trp Tyr Asp Ala Ala Asn Glu Ile Val Asn
                140                 145                 150

AAT TCA GAT GCT TAT ACA GCA GAA TCA ATT CAG CCG TTG TAT AAG TTA       1012
Asn Ser Asp Ala Tyr Thr Ala Glu Ser Ile Gln Pro Leu Tyr Lys Leu
155                 160                 165

ATT AAT GAT GCA TAC GAT GTG TTA GAA TCA AAA GAT TAC AGT AAG TAT       1060
Ile Asn Asp Ala Tyr Asp Val Leu Glu Ser Lys Asp Tyr Ser Lys Tyr
170                 175                 180                 185

GAT TCT CAA GAT AAA GTC AAC AAT CTT GCA GAT CAG TTG AGA GAT GCA       1108
Asp Ser Gln Asp Lys Val Asn Asn Leu Ala Asp Gln Leu Arg Asp Ala
                190                 195                 200

GTT CAG GCA GTT CAA CTA GAA GCA CCT ACA GTG ATT GAC GCA CCT GAA       1156
Val Gln Ala Val Gln Leu Glu Ala Pro Thr Val Ile Asp Ala Pro Glu
                205                 210                 215

CTA ACT CCA GCT TTG ACT ACT TAC AAA CTT GTT GTT AAA GGT AAC ACT       1204
Leu Thr Pro Ala Leu Thr Thr Tyr Lys Leu Val Val Lys Gly Asn Thr
                220                 225                 230

TTC TCA GGA GAA ACA ACT ACT AAA GCC ATC GAT ACT GCA ACT GCG GAA       1252
Phe Ser Gly Glu Thr Thr Thr Lys Ala Ile Asp Thr Ala Thr Ala Glu
                235                 240                 245

AAA GAA TTC AAA CAA TAC GCA ACA GCT AAC AAT GTT GAC GGT GAG TGG       1300
Lys Glu Phe Lys Gln Tyr Ala Thr Ala Asn Asn Val Asp Gly Glu Trp
250                 255                 260                 265

TCT TAT GAC GAT GCA ACT AAA ACC TTT ACA GTT ACT GAA AAA CCA GCA       1348
Ser Tyr Asp Asp Ala Thr Lys Thr Phe Thr Val Thr Glu Lys Pro Ala
```

-continued

```
                      270                 275                 280
GTG ATT GAC GCA CCT GAA CTA ACT CCA GCC TTG ACT ACT TAC AAA CTT        1396
Val Ile Asp Ala Pro Glu Leu Thr Pro Ala Leu Thr Thr Tyr Lys Leu
            285                 290                 295

ATT GTT AAA GGT AAC ACT TTC TCA GGC GAA ACA ACT ACT AAA GCA GTA        1444
Ile Val Lys Gly Asn Thr Phe Ser Gly Glu Thr Thr Thr Lys Ala Val
            300                 305                 310

GAC GCA GAA ACT GCA GAA AAA GCC TTC AAA CAA TAC GCA ACA GCT AAC        1492
Asp Ala Glu Thr Ala Glu Lys Ala Phe Lys Gln Tyr Ala Thr Ala Asn
            315                 320                 325

AAT GTT GAC GGT GAG TGG TCT TAT GAC GAT GCA ACT AAA ACC TTT ACA        1540
Asn Val Asp Gly Glu Trp Ser Tyr Asp Asp Ala Thr Lys Thr Phe Thr
330                 335                 340                 345

GTT ACT GAA AAA CCA GCA GTG ATT GAC GCA CCT GAA CTA ACT CCA GCC        1588
Val Thr Glu Lys Pro Ala Val Ile Asp Ala Pro Glu Leu Thr Pro Ala
            350                 355                 360

TTG ACT ACT TAC AAA CTT ATT GTT AAA GGT AAC ACT TTC TCA GGC GAA        1636
Leu Thr Thr Tyr Lys Leu Ile Val Lys Gly Asn Thr Phe Ser Gly Glu
            365                 370                 375

ACA ACT ACT AAA GCT ATC GAT GCT GCA ACT GCA GAA AAA GAA TTC AAA        1684
Thr Thr Thr Lys Ala Ile Asp Ala Ala Thr Ala Glu Lys Glu Phe Lys
            380                 385                 390

CAA TAC GCA ACA GCT AAC GGT GTT GAC GGT GAA TGG TCT TAT GAC GAT        1732
Gln Tyr Ala Thr Ala Asn Gly Val Asp Gly Glu Trp Ser Tyr Asp Asp
395                 400                 405

GCA ACT AAA ACC TTT ACA GTT ACT GAA AAA CCA GCA GTG ATT GAC GCA        1780
Ala Thr Lys Thr Phe Thr Val Thr Glu Lys Pro Ala Val Ile Asp Ala
410                 415                 420                 425

CCT GAA CTA ACT CCA GCC TTG ACT ACT TAC AAA CTT ATT GTT AAA GGT        1828
Pro Glu Leu Thr Pro Ala Leu Thr Thr Tyr Lys Leu Ile Val Lys Gly
            430                 435                 440

AAC ACT TTC TCA GGC GAA ACA ACT ACT AAA GCA GTA GAC GCA GAA ACT        1876
Asn Thr Phe Ser Gly Glu Thr Thr Thr Lys Ala Val Asp Ala Glu Thr
            445                 450                 455

GCA GAA AAA GCC TTC AAA CAA TAC GCT AAC GAA AAC GGT GTT TAC GGT        1924
Ala Glu Lys Ala Phe Lys Gln Tyr Ala Asn Glu Asn Gly Val Tyr Gly
            460                 465                 470

GAA TGG TCT TAT GAC GAT GCA ACT AAA ACC TTT ACA GTT ACT GAA AAA        1972
Glu Trp Ser Tyr Asp Asp Ala Thr Lys Thr Phe Thr Val Thr Glu Lys
            475                 480                 485

CCA GCA GTG ATT GAC GCA CCT GAA TTA ACA CCA GCA TTG ACA ACC TAC        2020
Pro Ala Val Ile Asp Ala Pro Glu Leu Thr Pro Ala Leu Thr Thr Tyr
490                 495                 500                 505

AAA CTT GTT ATC AAT GGT AAA ACA TTG AAA GGC GAA ACA ACT ACT AAA        2068
Lys Leu Val Ile Asn Gly Lys Thr Leu Lys Gly Glu Thr Thr Thr Lys
            510                 515                 520

GCA GTA GAC GCA GAA ACT GCA GAA AAA GCC TTC AAA CAA TAC GCT AAC        2116
Ala Val Asp Ala Glu Thr Ala Glu Lys Ala Phe Lys Gln Tyr Ala Asn
            525                 530                 535

GAA AAC GGT GTT GAT GGT GTT TGG ACT TAC GAT GAT GCG ACT AAG ACC        2164
Glu Asn Gly Val Asp Gly Val Trp Thr Tyr Asp Asp Ala Thr Lys Thr
            540                 545                 550

TTT ACG GTA ACT GAA ATG GTT ACT GAA GTT CCT GGT GAT GCA CCA ACT        2212
Phe Thr Val Thr Glu Met Val Thr Glu Val Pro Gly Asp Ala Pro Thr
            555                 560                 565

GAA CCA GAA AAG CCA GAA GCA AGT ATC CCT CTT GTT CCG TTA ACT CCT        2260
Glu Pro Glu Lys Pro Glu Ala Ser Ile Pro Leu Val Pro Leu Thr Pro
570                 575                 580                 585

GCA ACT CCA ATT GCT AAA GAT GAC GCT AAG AAA GAC GAT ACT AAG AAA        2308
```

```
Ala Thr Pro Ile Ala Lys Asp Asp Ala Lys Lys Asp Asp Thr Lys Lys
                590                 595                 600

GTC GAT ACT AAG AAA GAA GAC GCT AAA AAA CCA GAA GCT AAG AAA GAA         2356
Val Asp Thr Lys Lys Glu Asp Ala Lys Lys Pro Glu Ala Lys Lys Glu
            605                 610                 615

GAA GCT AAG AAA GAA GAA GCT AAG AAA GCT GCA ACT CTT CCT ACA ACT         2404
Glu Ala Lys Lys Glu Glu Ala Lys Lys Ala Ala Thr Leu Pro Thr Thr
        620                 625                 630

GGT GAA GGA AGC AAC CCA TTT TTC ACA GCT GCT GCG CTT GCA GTA ATG         2452
Gly Glu Gly Ser Asn Pro Phe Phe Thr Ala Ala Ala Leu Ala Val Met
    635                 640                 645

GCT GGT GCG GGT GCT TTG GCA GTC GCT TCA AAA CGT AAA GAA GAC             2497
Ala Gly Ala Gly Ala Leu Ala Val Ala Ser Lys Arg Lys Glu Asp
650                 655                 660

TAATTGTCAT TGCTTTTGAC AAAAAGCTT                                         2526

(2) INFORMATION FOR SEQ ID NO:2:

(i) SEQUENCE CHARACTERISTICS:
        (A) LENGTH: 664 amino acids
        (B) TYPE: amino acid
        (D) TOPOLOGY: linear (ii) MOLECULE TYPE: protein (xi) SEQUENCE DESCRIPTION: SEQ ID NO:2:

Met Glu Lys Glu Lys Lys Val Lys Tyr Phe Leu Arg Lys Ser Ala Phe
1               5                   10                  15

Gly Leu Ala Ser Val Ser Ala Ala Phe Leu Val Ser Gly Ala Leu Glu
                20                  25                  30

Asn Thr Ile Thr Val Ser Ala Glu Thr Ile Pro Ala Ala Val Ile Val
            35                  40                  45

Pro Val Gly Leu Asp Thr Thr Glu Leu Gln Lys Trp Tyr Asp Ile Ala
        50                  55                  60

Asn Asp Leu Val Ala Thr Asp Asn Ala Thr Pro Gly Gly Val Phe Thr
65                  70                  75                  80

Ala Asp Ser Met Lys Ala Leu Tyr Arg Leu Leu Asn Asp Ala Tyr Asp
                85                  90                  95

Val Leu Glu Ser Lys Asp Tyr Arg Lys Tyr Asp Ser Gln Asp Arg Ile
                100                 105                 110

Val Glu Leu Val Asn Asn Leu Lys Asn Thr Thr Gln Ser Leu Leu Pro
            115                 120                 125

Ile Gly Val Glu Pro Val Val Phe Asp Thr Thr Arg Leu Asn Thr Trp
        130                 135                 140

Tyr Asp Ala Ala Asn Glu Ile Val Asn Asn Ser Asp Ala Tyr Thr Ala
145                 150                 155                 160

Glu Ser Ile Gln Pro Leu Tyr Lys Leu Ile Asn Asp Ala Tyr Asp Val
                165                 170                 175

Leu Glu Ser Lys Asp Tyr Ser Lys Tyr Asp Ser Gln Asp Lys Val Asn
                180                 185                 190

Asn Leu Ala Asp Gln Leu Arg Asp Ala Val Gln Ala Val Gln Leu Glu
            195                 200                 205

Ala Pro Thr Val Ile Asp Ala Pro Glu Leu Thr Pro Ala Leu Thr Thr
        210                 215                 220

Tyr Lys Leu Val Val Lys Gly Asn Thr Phe Ser Gly Glu Thr Thr Thr
225                 230                 235                 240

Lys Ala Ile Asp Thr Ala Thr Ala Glu Lys Glu Phe Lys Gln Tyr Ala
```

```
                        245                 250                 255
Thr Ala Asn Asn Val Asp Gly Glu Trp Ser Tyr Asp Asp Ala Thr Lys
                260                 265                 270

Thr Phe Thr Val Thr Glu Lys Pro Ala Val Ile Asp Ala Pro Glu Leu
            275                 280                 285

Thr Pro Ala Leu Thr Thr Tyr Lys Leu Ile Val Lys Gly Asn Thr Phe
        290                 295                 300

Ser Gly Glu Thr Thr Thr Lys Ala Val Asp Ala Glu Thr Ala Glu Lys
305                 310                 315                 320

Ala Phe Lys Gln Tyr Ala Thr Ala Asn Asn Val Asp Gly Glu Trp Ser
                325                 330                 335

Tyr Asp Asp Ala Thr Lys Thr Phe Thr Val Thr Glu Lys Pro Ala Val
            340                 345                 350

Ile Asp Ala Pro Glu Leu Thr Pro Ala Leu Thr Thr Tyr Lys Leu Ile
        355                 360                 365

Val Lys Gly Asn Thr Phe Ser Gly Glu Thr Thr Thr Lys Ala Ile Asp
    370                 375                 380

Ala Ala Thr Ala Glu Lys Glu Phe Lys Gln Tyr Ala Thr Ala Asn Gly
385                 390                 395                 400

Val Asp Gly Glu Trp Ser Tyr Asp Asp Ala Thr Lys Thr Phe Thr Val
                405                 410                 415

Thr Glu Lys Pro Ala Val Ile Asp Ala Pro Glu Leu Thr Pro Ala Leu
            420                 425                 430

Thr Thr Tyr Lys Leu Ile Val Lys Gly Asn Thr Phe Ser Gly Glu Thr
        435                 440                 445

Thr Thr Lys Ala Val Asp Ala Glu Thr Ala Glu Lys Ala Phe Lys Gln
    450                 455                 460

Tyr Ala Asn Glu Asn Gly Val Tyr Gly Glu Trp Ser Tyr Asp Asp Ala
465                 470                 475                 480

Thr Lys Thr Phe Thr Val Thr Glu Lys Pro Ala Val Ile Asp Ala Pro
                485                 490                 495

Glu Leu Thr Pro Ala Leu Thr Thr Tyr Lys Leu Val Ile Asn Gly Lys
            500                 505                 510

Thr Leu Lys Gly Glu Thr Thr Thr Lys Ala Val Asp Ala Glu Thr Ala
        515                 520                 525

Glu Lys Ala Phe Lys Gln Tyr Ala Asn Glu Asn Gly Val Asp Gly Val
    530                 535                 540

Trp Thr Tyr Asp Asp Ala Thr Lys Thr Phe Thr Val Thr Glu Met Val
545                 550                 555                 560

Thr Glu Val Pro Gly Asp Ala Pro Thr Glu Pro Glu Lys Pro Glu Ala
                565                 570                 575

Ser Ile Pro Leu Val Pro Leu Thr Pro Ala Thr Pro Ile Ala Lys Asp
            580                 585                 590

Asp Ala Lys Lys Asp Asp Thr Lys Lys Val Asp Thr Lys Lys Glu Asp
        595                 600                 605

Ala Lys Lys Pro Glu Ala Lys Lys Glu Glu Ala Lys Lys Glu Glu Ala
    610                 615                 620

Lys Lys Ala Ala Thr Leu Pro Thr Thr Gly Glu Gly Ser Asn Pro Phe
625                 630                 635                 640

Phe Thr Ala Ala Ala Leu Ala Val Met Ala Gly Ala Gly Ala Leu Ala
                645                 650                 655

Val Ala Ser Lys Arg Lys Glu Asp
            660
```

(2) INFORMATION FOR SEQ ID NO:3:

(i) SEQUENCE CHARACTERISTICS:
        (A) LENGTH: 508 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 3..506

(ix) FEATURE:
        (A) NAME/KEY: mat_peptide
        (B) LOCATION: 3..506

(xi) SEQUENCE DESCRIPTION: SEQ ID NO:3:

```
CT GCG TTT TTA GTT GGG ACT GCG GTA GTA AAT GCG GAA GAG TCA ACT        47
   Ala Phe Leu Val Gly Thr Ala Val Val Asn Ala Glu Glu Ser Thr
    1               5                  10                  15

GTT TCG CCT GTG ACA GTT GCT ACA GAT GCA GTT ACT ACT TCT AAG GAA        95
Val Ser Pro Val Thr Val Ala Thr Asp Ala Val Thr Thr Ser Lys Glu
                 20                  25                  30

GCG CTT GCG ATA ATT AAC AAG CTA AGT GAA GAT AAT TTA AAT AAT CTT       143
Ala Leu Ala Ile Ile Asn Lys Leu Ser Glu Asp Asn Leu Asn Asn Leu
             35                  40                  45

GAC ATC CAG GAA GTA TTG GCC AAA GCG GGG AGG GAC ATT TTA GCC TCT       191
Asp Ile Gln Glu Val Leu Ala Lys Ala Gly Arg Asp Ile Leu Ala Ser
         50                  55                  60

GAC TCA GCA GAT ACT ATC AAA GCA CTT CTT GCT GAA GTT ACC GCT GAA       239
Asp Ser Ala Asp Thr Ile Lys Ala Leu Leu Ala Glu Val Thr Ala Glu
     65                  70                  75

GTT ACT CGT TTG AAT GAG GAA AAG ATG GCA CGT GAT GCA GTA GAC AAA       287
Val Thr Arg Leu Asn Glu Glu Lys Met Ala Arg Asp Ala Val Asp Lys
 80                  85                  90                  95

GCT ATT GCA GCA GAT GCA GCC GCT TTT TCT GAA TTA AAA GAT GCT CAA       335
Ala Ile Ala Ala Asp Ala Ala Ala Phe Ser Glu Leu Lys Asp Ala Gln
                100                 105                 110

CTG AAA GCA TAT GAA GAT CTT GCG AAA CTC GCA GCA GAT ACA GAC TTA       383
Leu Lys Ala Tyr Glu Asp Leu Ala Lys Leu Ala Ala Asp Thr Asp Leu
            115                 120                 125

GAT TTA GAT GTT GCT AAA ATT ATA AAT GAC TAC ACT ACA AAA GTT GAA       431
Asp Leu Asp Val Ala Lys Ile Ile Asn Asp Tyr Thr Thr Lys Val Glu
        130                 135                 140

AAT GCA AAA ACA GCA GAA GAT GTT AAA AAA ATT TTT GAA GAA TCT CAA       479
Asn Ala Lys Thr Ala Glu Asp Val Lys Lys Ile Phe Glu Glu Ser Gln
    145                 150                 155

AAT GAA GTG ACA CGT ATT AAA ACA GAA AA                                508
Asn Glu Val Thr Arg Ile Lys Thr Glu
160                 165
```

(2) INFORMATION FOR SEQ ID NO:4:

(i) SEQUENCE CHARACTERISTICS:
        (A) LENGTH: 168 amino acids
        (B) TYPE: amino acid
        (D) TOPOLOGY: linear (ii) MOLECULE TYPE: protein (xi) SEQUENCE DESCRIPTION: SEQ ID NO:4:

```
Ala Phe Leu Val Gly Thr Ala Val Val Asn Ala Glu Glu Ser Thr Val
 1               5                  10                  15
```

```
Ser Pro Val Thr Val Ala Thr Asp Ala Val Thr Thr Ser Lys Glu Ala
         20                  25                  30

Leu Ala Ile Ile Asn Lys Leu Ser Glu Asp Asn Leu Asn Asn Leu Asp
     35                  40                  45

Ile Gln Glu Val Leu Ala Lys Ala Gly Arg Asp Ile Leu Ala Ser Asp
 50                  55                  60

Ser Ala Asp Thr Ile Lys Ala Leu Leu Ala Glu Val Thr Ala Glu Val
 65                  70                  75                  80

Thr Arg Leu Asn Glu Glu Lys Met Ala Arg Asp Ala Val Asp Lys Ala
                 85                  90                  95

Ile Ala Ala Asp Ala Ala Ala Phe Ser Glu Leu Lys Asp Ala Gln Leu
                100                 105                 110

Lys Ala Tyr Glu Asp Leu Ala Lys Leu Ala Ala Asp Thr Asp Leu Asp
            115                 120                 125

Leu Asp Val Ala Lys Ile Ile Asn Asp Tyr Thr Thr Lys Val Glu Asn
130                 135                 140

Ala Lys Thr Ala Glu Asp Val Lys Lys Ile Phe Glu Glu Ser Gln Asn
145                 150                 155                 160

Glu Val Thr Arg Ile Lys Thr Glu
                165

(2) INFORMATION FOR SEQ ID NO:5:

(i) SEQUENCE CHARACTERISTICS:
        (A) LENGTH: 519 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 3..518

(ix) FEATURE:
        (A) NAME/KEY: mat_peptide
        (B) LOCATION: 3..518

(xi) SEQUENCE DESCRIPTION: SEQ ID NO:5:

CT GCG TTT TTA GTT TCG GGA GCA CTA GAA AAT ACT ATA ACT GTT TCT         47
   Ala Phe Leu Val Ser Gly Ala Leu Glu Asn Thr Ile Thr Val Ser
   1               5                  10                  15

GCA GAA ACT ATA CCT GCA GCG GTC ATT GTA CCT GTT GGC CTA GAT ACT        95
Ala Glu Thr Ile Pro Ala Ala Val Ile Val Pro Val Gly Leu Asp Thr
                 20                  25                  30

ACA GAA TTA CAA AAA TGG TAT GAC ATT GCA AAT GAT TTA GTT GCG ACT       143
Thr Glu Leu Gln Lys Trp Tyr Asp Ile Ala Asn Asp Leu Val Ala Thr
             35                  40                  45

GAC AAT GCT ACT CCG GGA GGC GTA TTT ACA GCA GAC TCA ATG AAG GCA       191
Asp Asn Ala Thr Pro Gly Gly Val Phe Thr Ala Asp Ser Met Lys Ala
         50                  55                  60

TTA TAT CGT TTA CTA AAT GAT GCA TAC GAT GTG TTG GAA TCA AAA GAC       239
Leu Tyr Arg Leu Leu Asn Asp Ala Tyr Asp Val Leu Glu Ser Lys Asp
 65                  70                  75

TAT AGA AAA TAT GAT TCT CAA GAT AGG ATT GTT GAA TTG GTA AAC AAT       287
Tyr Arg Lys Tyr Asp Ser Gln Asp Arg Ile Val Glu Leu Val Asn Asn
 80                  85                  90                  95

TTA AAG AAT ACT ACG CAG TCT CTT TTA CCA ATT GGA GTA GAA CCA GTA       335
Leu Lys Asn Thr Thr Gln Ser Leu Leu Pro Ile Gly Val Glu Pro Val
                 100                 105                 110

GTA TTT GAT ACT ACT CGC TTG AAT ACC TGG TAT GAT GCT GCT AAT GAA       383
Val Phe Asp Thr Thr Arg Leu Asn Thr Trp Tyr Asp Ala Ala Asn Glu
```

```
                   115                 120                 125
ATT GTT AAT AAT TCA GAT GCT TAT ACA GCA GAA TCA ATT CAG CCG TTG        431
Ile Val Asn Asn Ser Asp Ala Tyr Thr Ala Glu Ser Ile Gln Pro Leu
        130                 135                 140

TAT AAG TTA ATT AAT GAT GCA TAC GAT GTG TTA GAA TCA AAA GAT TAC        479
Tyr Lys Leu Ile Asn Asp Ala Tyr Asp Val Leu Glu Ser Lys Asp Tyr
145                 150                 155

AGT AAG TAT GAT TCT CAA GAT AAA GTC AAC AAT CTT GCA G                  519
Ser Lys Tyr Asp Ser Gln Asp Lys Val Asn Asn Leu Ala
160                 165                 170
```

(2) INFORMATION FOR SEQ ID NO:6:

(i) SEQUENCE CHARACTERISTICS:
        (A) LENGTH: 172 amino acids
        (B) TYPE: amino acid
        (D) TOPOLOGY: linear (ii) MOLECULE TYPE: protein (xi) SEQUENCE DESCRIPTION: SEQ ID NO:6:

```
Ala Phe Leu Val Ser Gly Ala Leu Glu Asn Thr Ile Thr Val Ser Ala
 1               5                  10                  15

Glu Thr Ile Pro Ala Ala Val Ile Val Pro Val Gly Leu Asp Thr Thr
             20                  25                  30

Glu Leu Gln Lys Trp Tyr Asp Ile Ala Asn Asp Leu Val Ala Thr Asp
         35                  40                  45

Asn Ala Thr Pro Gly Gly Val Phe Thr Ala Asp Ser Met Lys Ala Leu
     50                  55                  60

Tyr Arg Leu Leu Asn Asp Ala Tyr Asp Val Leu Glu Ser Lys Asp Tyr
65                  70                  75                  80

Arg Lys Tyr Asp Ser Gln Asp Arg Ile Val Glu Leu Val Asn Asn Leu
                 85                  90                  95

Lys Asn Thr Thr Gln Ser Leu Leu Pro Ile Gly Val Glu Pro Val Val
             100                 105                 110

Phe Asp Thr Thr Arg Leu Asn Thr Trp Tyr Asp Ala Ala Asn Glu Ile
         115                 120                 125

Val Asn Asn Ser Asp Ala Tyr Thr Ala Glu Ser Ile Gln Pro Leu Tyr
     130                 135                 140

Lys Leu Ile Asn Asp Ala Tyr Asp Val Leu Glu Ser Lys Asp Tyr Ser
145                 150                 155                 160

Lys Tyr Asp Ser Gln Asp Lys Val Asn Asn Leu Ala
                 165                 170
```

(2) INFORMATION FOR SEQ ID NO:7:

(i) SEQUENCE CHARACTERISTICS:
        (A) LENGTH: 519 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..519

(ix) FEATURE:
        (A) NAME/KEY: mat_peptide
        (B) LOCATION: 1..519

(xi) SEQUENCE DESCRIPTION: SEQ ID NO:7:

```
TCT TCA GTG GGT GCT CTA GAT GCT ACA ACG GTG TTA GAG CCT ACA ACA        48
```

```
Ser Ser Val Gly Ala Leu Asp Ala Thr Thr Val Leu Glu Pro Thr Thr
 1               5                  10                  15

GCC TTC ATT AGA GAG GCT GTT AGG GAA ATC AAT CAG CTT AGT GAT GAC      96
Ala Phe Ile Arg Glu Ala Val Arg Glu Ile Asn Gln Leu Ser Asp Asp
                20                  25                  30

TAC GCT GAC AAT CAA GAG CTT CAG GCT GTT CTT GCT AAT GCT GGA GTT     144
Tyr Ala Asp Asn Gln Glu Leu Gln Ala Val Leu Ala Asn Ala Gly Val
            35                  40                  45

GAG GCA CTT GCT GCA GAT ACT GTT GAT CAA GCC AAA GCA GCT CTT GAC     192
Glu Ala Leu Ala Ala Asp Thr Val Asp Gln Ala Lys Ala Ala Leu Asp
        50                  55                  60

AAA GCA AAG GCA GCT GTT GCT GGT GTT CAG CTT GAT GAA GCA AGA CGT     240
Lys Ala Lys Ala Ala Val Ala Gly Val Gln Leu Asp Glu Ala Arg Arg
 65                  70                  75                  80

GAG GCT TAC AGA ACA ATC AAT GCC TTA AGT GAT CAG CAC GAA AGC GAT     288
Glu Ala Tyr Arg Thr Ile Asn Ala Leu Ser Asp Gln His Glu Ser Asp
                85                  90                  95

CAA AAG GTT CAG CTA GCT CTA GTT GCT GCA GCA GCT AAG GTG GCA GAT     336
Gln Lys Val Gln Leu Ala Leu Val Ala Ala Ala Ala Lys Val Ala Asp
            100                 105                 110

GCT GCT TCA GTT GAT CAA GTG AAT GCA GCC ATT AAT GAT GCT CAT ACA     384
Ala Ala Ser Val Asp Gln Val Asn Ala Ala Ile Asn Asp Ala His Thr
        115                 120                 125

GCT ATT GCG GAC ATT ACA GGA GCA GCC TTG TTG GAG GCT AAA GAA GCT     432
Ala Ile Ala Asp Ile Thr Gly Ala Ala Leu Leu Glu Ala Lys Glu Ala
130                 135                 140

GCT ATC AAT GAA CTA AAG CAG TAT GGC ATT AGT GAT TAC TAT GTG ACC     480
Ala Ile Asn Glu Leu Lys Gln Tyr Gly Ile Ser Asp Tyr Tyr Val Thr
145                 150                 155                 160

TTA ATC AAC AAA GCC AAA ACT GTT GAA GGT GTC AAT GCG                 519
Leu Ile Asn Lys Ala Lys Thr Val Glu Gly Val Asn Ala
                165                 170
```

(2) INFORMATION FOR SEQ ID NO:8:

(i) SEQUENCE CHARACTERISTICS:
        (A) LENGTH: 173 amino acids
        (B) TYPE: amino acid
        (D) TOPOLOGY: linear (ii) MOLECULE TYPE: protein (xi) SEQUENCE DESCRIPTION: SEQ ID NO:8:

```
Ser Ser Val Gly Ala Leu Asp Ala Thr Thr Val Leu Glu Pro Thr Thr
 1               5                  10                  15

Ala Phe Ile Arg Glu Ala Val Arg Glu Ile Asn Gln Leu Ser Asp Asp
                20                  25                  30

Tyr Ala Asp Asn Gln Glu Leu Gln Ala Val Leu Ala Asn Ala Gly Val
            35                  40                  45

Glu Ala Leu Ala Ala Asp Thr Val Asp Gln Ala Lys Ala Ala Leu Asp
        50                  55                  60

Lys Ala Lys Ala Ala Val Ala Gly Val Gln Leu Asp Glu Ala Arg Arg
 65                  70                  75                  80

Glu Ala Tyr Arg Thr Ile Asn Ala Leu Ser Asp Gln His Glu Ser Asp
                85                  90                  95

Gln Lys Val Gln Leu Ala Leu Val Ala Ala Ala Ala Lys Val Ala Asp
            100                 105                 110

Ala Ala Ser Val Asp Gln Val Asn Ala Ala Ile Asn Asp Ala His Thr
        115                 120                 125
```

```
Ala Ile Ala Asp Ile Thr Gly Ala Ala Leu Leu Glu Ala Lys Glu Ala
        130                 135                 140

Ala Ile Asn Glu Leu Lys Gln Tyr Gly Ile Ser Asp Tyr Tyr Val Thr
145                 150                 155                 160

Leu Ile Asn Lys Ala Lys Thr Val Glu Gly Val Asn Ala
                165                 170

(2) INFORMATION FOR SEQ ID NO:9:

(i) SEQUENCE CHARACTERISTICS:
        (A) LENGTH: 1555 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 288..1526

(ix) FEATURE:
        (A) NAME/KEY: mat_peptide
        (B) LOCATION: 288..1526

(xi) SEQUENCE DESCRIPTION: SEQ ID NO:9:

AAGCTTTATT TTATTATAAA AGAAAGTAAT TTTTGAAAAA TTATAGAAAA TCACTTTTAT      60

GCTAATAAAA TAGCCATAAA TATAAATTGA TGAGTCTATG ATAGGAGATT TATTTGCCAG     120

GATTTCCTAA TTTTATTAAT TTAACGAAAA TTGATAGAAA AATTAAATGA AATCCTTGAT     180

TTAATTTTGT TAAGTTGTAT AATAAAAGGT GAAATTATTA GATTGTAGTT TCAAATTTTT     240

TGGTTTTTTA ATATGTGCTG GCGTATTAAA TAAAAAAGGA GAAAGTA ATG GAA AAA       296
                                                 Met Glu Lys
                                                   1

GAA AAA AAA GTA AAA TAC TTT TTA CGT AAA TCA GCT TTT GGA TTA GCG      344
Glu Lys Lys Val Lys Tyr Phe Leu Arg Lys Ser Ala Phe Gly Leu Ala
      5                  10                  15

TCC GTA TCA GCT GCG TTT TTA GTT GGG ACT GCG GTA GTA AAT GCG GAA      392
Ser Val Ser Ala Ala Phe Leu Val Gly Thr Ala Val Val Asn Ala Glu
 20                  25                  30                  35

GAG TCA ACT GTT TCG CCT GTG ACA GTT GCT ACA GAT GCA GTT ACT ACT      440
Glu Ser Thr Val Ser Pro Val Thr Val Ala Thr Asp Ala Val Thr Thr
                 40                  45                  50

TCT AAG GAA GCG CTT GCG ATA ATT AAC AAG CTA AGT GAA GAT AAT TTA      488
Ser Lys Glu Ala Leu Ala Ile Ile Asn Lys Leu Ser Glu Asp Asn Leu
         55                  60                  65

AAT AAT CTT GAC ATC CAG GAA GTA TTG GCC AAA GCG GGG AGG GAC ATT      536
Asn Asn Leu Asp Ile Gln Glu Val Leu Ala Lys Ala Gly Arg Asp Ile
     70                  75                  80

TTA GCC TCT GAC TCA GCA GAT ACT ATC AAA GCA CTT CTT GCT GAA GTT      584
Leu Ala Ser Asp Ser Ala Asp Thr Ile Lys Ala Leu Leu Ala Glu Val
 85                  90                  95

ACC GCT GAA GTT ACT CGT TTG AAT GAG GAA AAG ATG GCA CGT GAT GCA      632
Thr Ala Glu Val Thr Arg Leu Asn Glu Glu Lys Met Ala Arg Asp Ala
100                 105                 110                 115

GTA GAC AAA GCT ATT GCA GCA GAT GCA GCC GCT TTT TCT GAA TTA AAA      680
Val Asp Lys Ala Ile Ala Ala Asp Ala Ala Ala Phe Ser Glu Leu Lys
                120                 125                 130

GAT GCT CAA CTG AAA GCA TAT GAA GAT CTT GCG AAA CTC GCA GCA GAT      728
Asp Ala Gln Leu Lys Ala Tyr Glu Asp Leu Ala Lys Leu Ala Ala Asp
            135                 140                 145

ACA GAC TTA GAT TTA GAT GTT GCT AAA ATT ATA AAT GAC TAC ACT ACA      776
Thr Asp Leu Asp Leu Asp Val Ala Lys Ile Ile Asn Asp Tyr Thr Thr
        150                 155                 160
```

```
AAA GTT GAA AAT GCA AAA ACA GCA GAA GAT GTT AAA AAA ATT TTT GAA      824
Lys Val Glu Asn Ala Lys Thr Ala Glu Asp Val Lys Lys Ile Phe Glu
165                 170                 175

GAA TCT CAA AAT GAA GTG ACA CGT ATT AAA ACA GAA AAA GCT TTA AAA      872
Glu Ser Gln Asn Glu Val Thr Arg Ile Lys Thr Glu Lys Ala Leu Lys
180                 185                 190                 195

GCT GCA GCA CTA GCT AAA GCA AAA GCA GAT GCT ATT GAA ATT CTG AAG      920
Ala Ala Ala Leu Ala Lys Ala Lys Ala Asp Ala Ile Glu Ile Leu Lys
                200                 205                 210

AAA TAC GGA ATT GGC GAT TAC TAT ATT AAA TTA ATT AAT AAT GGT AAA      968
Lys Tyr Gly Ile Gly Asp Tyr Tyr Ile Lys Leu Ile Asn Asn Gly Lys
                215                 220                 225

ACT GCA GAA GGT GTG ACT GCT CTT AAA GAT GAA ATT TTA GCT TCA AAA     1016
Thr Ala Glu Gly Val Thr Ala Leu Lys Asp Glu Ile Leu Ala Ser Lys
                230                 235                 240

CCA GCA GTG ATT GAC GCA CCT GAA TTA ACA CCA GCT TTG ACA ACC TAC     1064
Pro Ala Val Ile Asp Ala Pro Glu Leu Thr Pro Ala Leu Thr Thr Tyr
245                 250                 255

AAA CTT GTT ATC AAT GGT AAA ACA TTG AAA GGC GAA ACA ACT ACT AAA     1112
Lys Leu Val Ile Asn Gly Lys Thr Leu Lys Gly Glu Thr Thr Thr Lys
260                 265                 270                 275

GCA GTA GAC GCA GAA ACT GCA GAA AAA GCC TTC AAA CAA TAC GCT AAC     1160
Ala Val Asp Ala Glu Thr Ala Glu Lys Ala Phe Lys Gln Tyr Ala Asn
                280                 285                 290

GAA AAC GGT GTT GAT GGT GTT TGG ACT TAC GAT GAT GCG ACT AAG ACC     1208
Glu Asn Gly Val Asp Gly Val Trp Thr Tyr Asp Asp Ala Thr Lys Thr
                295                 300                 305

TTT ACT GTA ACT GAA ATG GTT ACT GAA GTT CCT GGT GAT GCA CCA ACT     1256
Phe Thr Val Thr Glu Met Val Thr Glu Val Pro Gly Asp Ala Pro Thr
                310                 315                 320

GAA CCA AAA AAA CCA GAA GCA AGT ATC CCT CTT GTT CCG TTA ACT CCT     1304
Glu Pro Lys Lys Pro Glu Ala Ser Ile Pro Leu Val Pro Leu Thr Pro
325                 330                 335

GCA ACT CCA ATT GCT AAA GAT GAC GCT AAG AAA GAC GAT ACT AAG AAA     1352
Ala Thr Pro Ile Ala Lys Asp Asp Ala Lys Lys Asp Asp Thr Lys Lys
340                 345                 350                 355

GAC GAT ACT AAG AAA GAA GAT GCT AAA AAA CCA GAA GCT AAG AAA GAA     1400
Asp Asp Thr Lys Lys Glu Asp Ala Lys Lys Pro Glu Ala Lys Lys Glu
                360                 365                 370

GAA GCT AAG AAA GCT GCA ACT CTT CCT ACA ACT GGT GAA GGA AGC AAC     1448
Glu Ala Lys Lys Ala Ala Thr Leu Pro Thr Thr Gly Glu Gly Ser Asn
                375                 380                 385

CCA TTC TTC ACA GCT GCT GCG CTT GCA GTA ATG GCT GGT GCG GGT GCT     1496
Pro Phe Phe Thr Ala Ala Ala Leu Ala Val Met Ala Gly Ala Gly Ala
                390                 395                 400

TTG GCA GTC GCT TCA AAA CGT AAA GAA GAC TAATTGTCAT TGCTTTTGAC       1546
Leu Ala Val Ala Ser Lys Arg Lys Glu Asp
                405                 410

AAAAAGCTT                                                           1555

(2) INFORMATION FOR SEQ ID NO:10:

(i) SEQUENCE CHARACTERISTICS:
        (A) LENGTH: 413 amino acids
        (B) TYPE: amino acid
        (D) TOPOLOGY: linear (ii) MOLECULE TYPE: protein (xi) SEQUENCE DESCRIPTION: SEQ ID NO:10:
```

```
Met Glu Lys Glu Lys Lys Val Lys Tyr Phe Leu Arg Lys Ser Ala Phe
 1               5                  10                  15

Gly Leu Ala Ser Val Ser Ala Ala Phe Leu Val Gly Thr Ala Val Val
             20                  25                  30

Asn Ala Glu Glu Ser Thr Val Ser Pro Val Thr Val Ala Thr Asp Ala
             35                  40                  45

Val Thr Thr Ser Lys Glu Ala Leu Ala Ile Ile Asn Lys Leu Ser Glu
 50                  55                  60

Asp Asn Leu Asn Asn Leu Asp Ile Gln Glu Val Leu Ala Lys Ala Gly
 65                  70                  75                  80

Arg Asp Ile Leu Ala Ser Asp Ser Ala Asp Thr Ile Lys Ala Leu Leu
                 85                  90                  95

Ala Glu Val Thr Ala Glu Val Thr Arg Leu Asn Glu Glu Lys Met Ala
             100                 105                 110

Arg Asp Ala Val Asp Lys Ala Ile Ala Ala Asp Ala Ala Phe Ser
             115                 120                 125

Glu Leu Lys Asp Ala Gln Leu Lys Ala Tyr Glu Asp Leu Ala Lys Leu
             130                 135                 140

Ala Ala Asp Thr Asp Leu Asp Leu Asp Val Ala Lys Ile Ile Asn Asp
145                 150                 155                 160

Tyr Thr Thr Lys Val Glu Asn Ala Lys Thr Ala Glu Asp Val Lys Lys
                 165                 170                 175

Ile Phe Glu Glu Ser Gln Asn Glu Val Thr Arg Ile Lys Thr Glu Lys
             180                 185                 190

Ala Leu Lys Ala Ala Ala Leu Ala Lys Ala Lys Ala Asp Ala Ile Glu
             195                 200                 205

Ile Leu Lys Lys Tyr Gly Ile Gly Asp Tyr Tyr Ile Lys Leu Ile Asn
             210                 215                 220

Asn Gly Lys Thr Ala Glu Gly Val Thr Ala Leu Lys Asp Glu Ile Leu
225                 230                 235                 240

Ala Ser Lys Pro Ala Val Ile Asp Ala Pro Glu Leu Thr Pro Ala Leu
             245                 250                 255

Thr Thr Tyr Lys Leu Val Ile Asn Gly Lys Thr Leu Lys Gly Glu Thr
             260                 265                 270

Thr Thr Lys Ala Val Asp Ala Glu Thr Ala Glu Lys Ala Phe Lys Gln
             275                 280                 285

Tyr Ala Asn Glu Asn Gly Val Asp Gly Val Trp Thr Tyr Asp Asp Ala
             290                 295                 300

Thr Lys Thr Phe Thr Val Thr Glu Met Val Thr Glu Val Pro Gly Asp
305                 310                 315                 320

Ala Pro Thr Glu Pro Lys Lys Pro Glu Ala Ser Ile Pro Leu Val Pro
             325                 330                 335

Leu Thr Pro Ala Thr Pro Ile Ala Lys Asp Asp Ala Lys Lys Asp Asp
             340                 345                 350

Thr Lys Lys Asp Asp Thr Lys Lys Glu Asp Ala Lys Lys Pro Glu Ala
             355                 360                 365

Lys Lys Glu Glu Ala Lys Lys Ala Ala Thr Leu Pro Thr Thr Gly Glu
             370                 375                 380

Gly Ser Asn Pro Phe Phe Thr Ala Ala Leu Ala Val Met Ala Gly
385                 390                 395                 400

Ala Gly Ala Leu Ala Val Ala Ser Lys Arg Lys Glu Asp
                 405                 410
```

```
(2) INFORMATION FOR SEQ ID NO:11:

(i) SEQUENCE CHARACTERISTICS:
        (A) LENGTH: 6 amino acids
        (B) TYPE: amino acid
        (D) TOPOLOGY: linear (ii) MOLECULE TYPE: protein (xi) SEQUENCE DESCRIPTION: SEQ ID NO:11:

Leu Pro Thr Thr Gly Glu
 1               5

(2) INFORMATION FOR SEQ ID NO:12:

(i) SEQUENCE CHARACTERISTICS:
        (A) LENGTH: 6 amino acids
        (B) TYPE: amino acid
        (D) TOPOLOGY: linear (ii) MOLECULE TYPE: protein (xi) SEQUENCE DESCRIPTION: SEQ ID NO:12:

Leu Pro Xaa Thr Gly Xaa
 1               5
```

We claim:

1. An isolated DNA molecule coding for a $f\alpha_2M$-binding protein or polypeptide obtained by:
   (a) partially digesting chromosomal DNA from streptococcal cells whereby DNA fragments are obtained;
   (b) ligating said DNA fragments into expression vectors;
   (c) packaging said expression vectors containing said ligated DNA into phage particles;
   (d) infecting *E. coli* cells with said phage particles to obtain a plurality of phage clones;
   (e) selecting from said plurality of phage clones the phage clones which react with $f\alpha_2M$;
   (f) and purifying the phage DNA from said selected phage clones to obtain said isolated DNA molecule,
   wherein said DNA molecule comprises the nucleotide sequence of SEQ ID NO:3, or a part thereof, the nucleotide sequence of SEQ ID NO:5, or a part thereof, or the nucleotide sequence of SEQ ID NO:7, or a part thereof, and wherein said DNA molecule encodes a protein or polypeptide with $f\alpha_2M$-binding activity.

2. The DNA molecule according to claim 1, wherein said DNA molecule comprises the nucleotide sequence of SEQ ID NO:3 or a part thereof encoding a protein or polypeptide with $f\alpha_2M$-binding activity.

3. The DNA molecule according to claim 1, wherein said DNA molecule comprises the nucleotide sequence of SEQ ID NO:5 or a part thereof encoding a protein or polypeptide with $f\alpha_2M$-binding activity.

4. The DNA molecule according to claim 1, wherein said DNA molecule comprises the nucleotide sequence of SEQ ID NO:7 or a part thereof encoding a protein or polypeptide with $f\alpha_2M$-binding activity.

5. A plasmid or phage containing a nucleotide sequence according to claim 1.

6. A microorganism containing at least one plasmid or phage according to claim 5.

7. A microorganism containing at least one isolated DNA molecule according to claim 1.

8. A method for producing a protein or polypeptide with $f\alpha_2M$-binding activity, comprising inserting at least one DNA molecule according to claim 1 in a microorganism, culturing said microorganism in a suitable medium, and isolating said protein or polypeptide by affinity chromatographic purification using an immobilized ligand.

9. A purified protein or a polypeptide having $f\alpha_2M$-binding activity, comprising an amino acid sequence encoded by an isolated DNA molecule, wherein said isolated DNA molecule is obtained by:
   (a) partially digesting chromosomal DNA from streptococcal cells whereby DNA fragments are obtained;
   (b) ligating said DNA fragments into expression vectors;
   (c) packaging said expression vectors containing said ligated DNA into phage particles;
   (d) infecting *E. coli* cells with said phage particles to obtain a plurality of phage clones;
   (e) selecting from said plurality of phage clones the phage clones which react with $f\alpha_2M$;
   (f) and purifying the phage DNA from said selected phage clones to obtain said isolated DNA molecule,
   wherein said DNA molecule comprises the nucleotide sequence of SEQ ID NO:3, or a part thereof, the nucleotide sequence of SEQ ID NO:5, or a part thereof, or the nucleotide sequence of SEQ ID NO:7, or a part thereof, and wherein said purified protein or polypeptide has $f\alpha_2M$-binding activity.

10. A purified protein or polypeptide according to claim 9, comprising a fusion protein.

11. A method of inhibiting the binding of $f\alpha_2M$ to streptococcal cells, comprising contacting said $f\alpha_2M$ in the presence of said streptococcal cells with a protein or a polypeptide according to claim 9.

12. An isolated DNA molecule, comprising the nucleotide sequence of SEQ ID NO:3 or a part thereof encoding a protein or polypeptide with $f\alpha_2M$-binding activity.

13. An isolated DNA molecule, comprising the nucleotide sequence of SEQ ID NO:5 or a part thereof encoding a protein or polypeptide with $f\alpha_2M$-binding activity.

14. An isolated DNA molecule, comprising the nucleotide sequence of SEQ ID NO:7 or a part thereof encoding a protein or polypeptide with $f\alpha_2M$-binding activity.

15. An isolated protein or polypeptide having $f\alpha_2M$-binding activity, comprising an amino acid sequence encoded by an isolated DNA molecule, wherein said isolated DNA molecule comprises the nucleotide sequence of SEQ ID NO:3 or a part thereof encoding a protein or polypeptide with $f\alpha_2M$-binding activity.

16. An isolated protein or polypeptide having $f\alpha_2M$-binding activity, comprising an amino acid sequence encoded by an isolated DNA molecule, wherein said isolated DNA molecule comprises the nucleotide sequence of SEQ ID NO:5 or a part thereof encoding a protein or polypeptide with $f\alpha_2M$-binding activity.

17. An isolated protein or polypeptide having $f\alpha_2M$-binding activity, comprising an amino acid sequence encoded by an isolated DNA molecule, wherein said isolated DNA molecule comprises the nucleotide sequence of SEQ ID NO:7 or a part thereof encoding a protein or polypeptide with $f\alpha_2M$-binding activity.

18. An isolated DNA molecule, whose natural source is streptococcal cells, coding for a $f_2\alpha M$-binding protein or polypeptide obtained by:
   (a) partially digesting chromosomal DNA from streptococcal cells whereby DNA fragments are obtained;
   (b) ligating said DNA fragments into expression vectors;
   (c) packaging said expression vectors containing said ligated DNA into phage particles;
   (d) infecting *E. coli* cells with said phage particles to obtain a plurality of phage clones;
   (e) selecting from said plurality of phage clones the phage clones which react with $f\alpha_2M$;
   (f) and purifying the phage DNA from said selected phage clones to obtain said isolated DNA molecule,
   wherein said DNA molecule comprises the nucleotide sequence of SEQ ID NO:3, or a part thereof, the nucleotide sequence of SEQ ID NO:5, or a part thereof, or the nucleotide sequence of SEQ ID NO:7, or a part thereof, and wherein said DNA molecule encodes a protein or polypeptide with $f\alpha_2M$-binding activity.

19. An isolated DNA molecule, whose natural source is streptococcal cells, coding for a $f\alpha_2M$-binding protein or polypeptide, wherein said DNA molecule comprises the nucleotide sequence of SEQ ID NO:3, or a part thereof, the nucleotide sequence of SEQ ID NO:5, or a part thereof, or the nucleotide sequence of SEO ID NO:7, or a part thereof, and wherein said DNA molecule encodes a protein or polypeptide with $f\alpha_2M$-binding activity.

20. An isolated protein or polypeptide encoded by an isolated DNA molecule. whose natural source is streptococcal cells, coding for a $f\alpha_2M$-binding protein or polypeptide, wherein said DNA molecule comprises the nucleotide sequence of SEQ ID NO:3, or a part thereof, the nucleotide sequence of SEQ ID NO:5, or a part thereof, or the nucleotide sequence of SEQ ID NO:7, or a part thereof, and wherein said DNA molecule encodes a protein or polypeptide with $f\alpha_2M$-binding activity.

21. An isolated DNA molecule comprising the nucleotide sequence of SEQ ID NO:3.

22. An isolated DNA molecule comprising the nucleotide sequence of SEQ ID NO:5.

23. An isolated DNA molecule comprising the nucleotide sequence of SEQ ID NO:7.

24. An isolated protein or polypeptide encoded by the nucleotide sequence of SEQ ID NO:3.

25. An isolated protein or polypeptide encoded by the nucleotide sequence of SEQ ID NO:5.

26. An isolated protein or polypeptide encoded by the nucleotide sequence of SEQ ID NO:7.

27. An isolated DNA molecule coding for a $f\alpha_2M$-binding protein or polypeptide, wherein said DNA molecule comprises the nucleotide sequence of SEQ ID NO:3, or a part thereof, the nucleotide sequence of SEQ ID NO:5, or a part thereof, or the nucleotide sequence of SEQ ID NO:7, or a part thereof.

28. A purified protein or a polypeptide having $f\alpha_2M$-binding activity, comprising an amino acid sequence encoded by a DNA molecule comprising the nucleotide sequence of SEQ ID NO:3, or a part thereof, the nucleotide sequence of SEQ ID NO:5, or a part thereof, or the nucleotide sequence of SEQ ID NO:7, or a part thereof.

* * * * *